(12) United States Patent
Berens et al.

(10) Patent No.: US 8,471,019 B2
(45) Date of Patent: Jun. 25, 2013

(54) QUINOID SYSTEMS AS ORGANIC SEMICONDUCTORS

(75) Inventors: Ulrich Berens, Binzen (DE); Arno Stassen, Hillegom (NL); Beat Schmidhalter, Bubendorf (CH); Wolfgang Kalb, Zürich (CH); Frank Bienewald, Hegenheim (FR)

(73) Assignee: BASF SE, Ludwigshafen (DE)

( * ) Notice: Subject to any disclaimer, the term of this patent is extended or adjusted under 35 U.S.C. 154(b) by 978 days.

(21) Appl. No.: 12/226,182

(22) PCT Filed: Apr. 4, 2007

(86) PCT No.: PCT/EP2007/053314
§ 371 (c)(1),
(2), (4) Date: Oct. 6, 2009

(87) PCT Pub. No.: WO2007/118799
PCT Pub. Date: Oct. 25, 2007

(65) Prior Publication Data
US 2009/0261321 A1 Oct. 22, 2009

(30) Foreign Application Priority Data

Apr. 13, 2006 (EP) .................................. 06112585

(51) Int. Cl.
| | |
|---|---|
| H01L 51/00 | (2006.01) |
| C07D 409/14 | (2006.01) |
| C07D 211/18 | (2006.01) |
| C07D 319/00 | (2006.01) |
| C07D 413/14 | (2006.01) |

(52) U.S. Cl.
USPC .................. 546/26; 546/50; 549/15; 549/16; 549/358; 549/359; 257/40

(58) Field of Classification Search
USPC ....... 546/26, 50; 549/15, 16, 358, 359; 437/1; 362/504; 544/69; 257/40
See application file for complete search history.

(56) References Cited

U.S. PATENT DOCUMENTS

| 5,028,643 A | 7/1991 | Jaffe ................................ 524/90 |
| 6,858,729 B2 * | 2/2005 | Hartmann et al. ............... 544/69 |
| 2004/0116700 A1 | 6/2004 | Hartmann et al. ............... 546/13 |

FOREIGN PATENT DOCUMENTS

| JP | 2000-231987 | 8/2000 |
| JP | 2002-124384 | 4/2002 |
| WO | 2006/120143 | 11/2006 |

OTHER PUBLICATIONS

Patent Abstracts of Japan Publication No. 2000231987, Aug. 22, 2000.
Patent Abstracts of Japan Publication No. 2002124384, Apr. 26, 2002.
T. Freund et al., Angew. Chem. Int. Ed. Engl. (1994), vol. 33, No. 23/24, pp. 2424-2426.
J. Mizuguchi, Dyes and Pigments, vol. 35, No. 4, (1997), pp. 347-360.
Patent Abstracts of Japan Publication No. 2004101560, Apr. 2, 2004.
Patent Abstracts of Japan Publication No. 2005250435, Sep. 15, 2005.

* cited by examiner

*Primary Examiner* — Andrew D Kosar
*Assistant Examiner* — Raymond Covington
(74) *Attorney, Agent, or Firm* — Shiela A. Loggins

(57) ABSTRACT

A semiconducting layer comprising a non-polymeric quinoid heteroacene compound of the formula (I) wherein X stands for O, S or NR, each of R, $R_1$, $R_2$, $R_3$, $R_4$, $R_5$, $R_6$, $R_7$, $R_8$ being independently selected from hydrogen and an organic residue, or 2 or more thereof together forming one or more annealed rings, which may be substituted or unsubstituted, carbocyclic or helerocyclic, aromatic, quinoid or aliphatic, may be used e.g. for the manufacture of a diode, an organic field effect transistor, an organic thin film transistor, or a device containing a diode and/or an organic field effect transistor and/or organic thin film transistor.

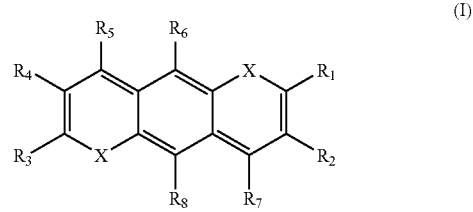

(I)

24 Claims, 5 Drawing Sheets

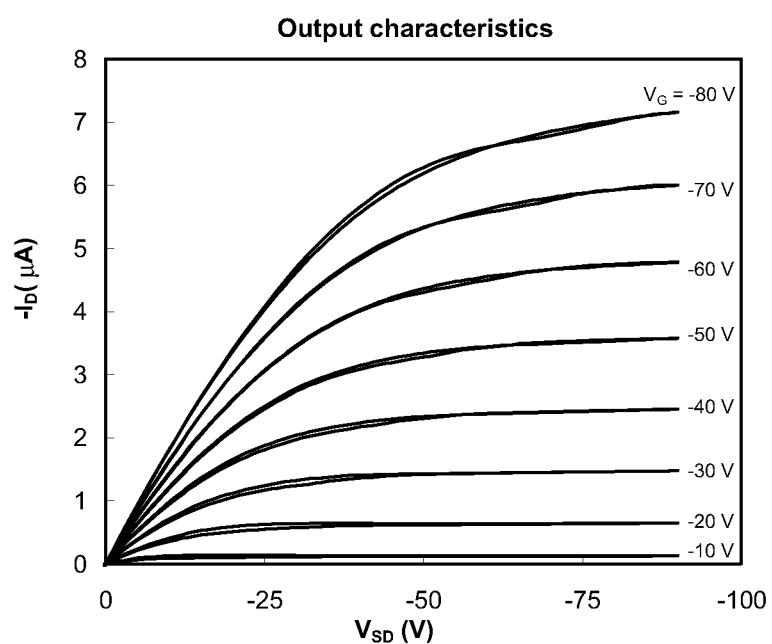
Fig. 1: Drain current ($I_D$) at constant gate voltage ($V_G$); transistor of example 4.

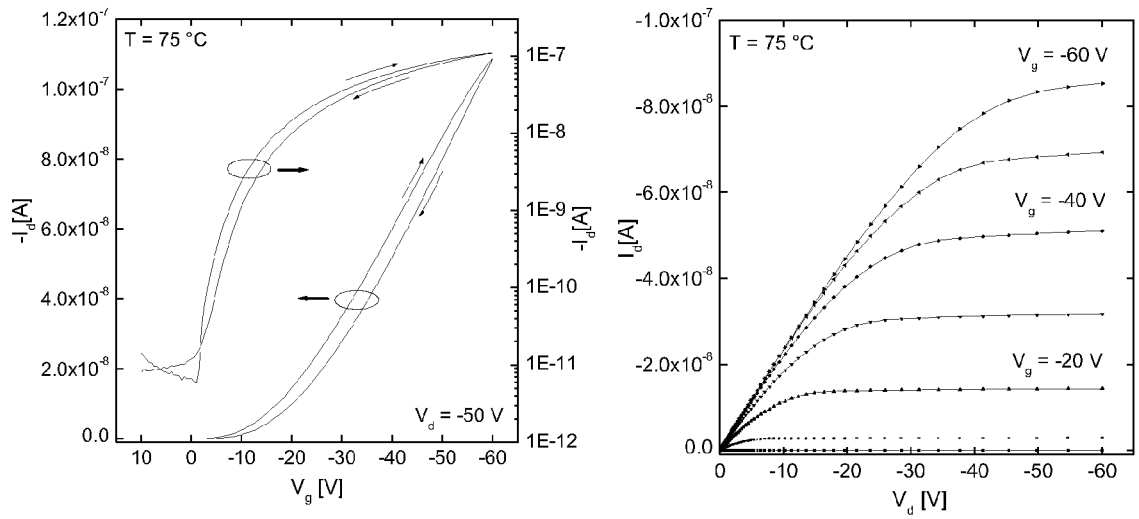
Fig. 2: Transfer characteristics both on a linear scale and on a logarithmic scale (left) and output characteristics (right); transistor of example 5a.
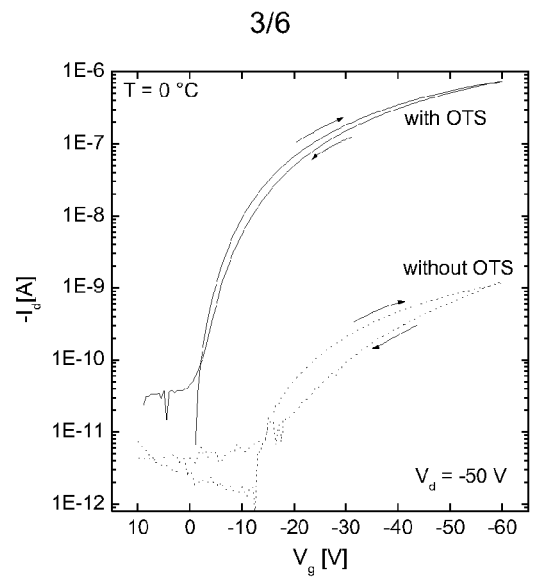
Fig. 3: TFT transfer characteristics with and without substrate surface treatment (example 7).

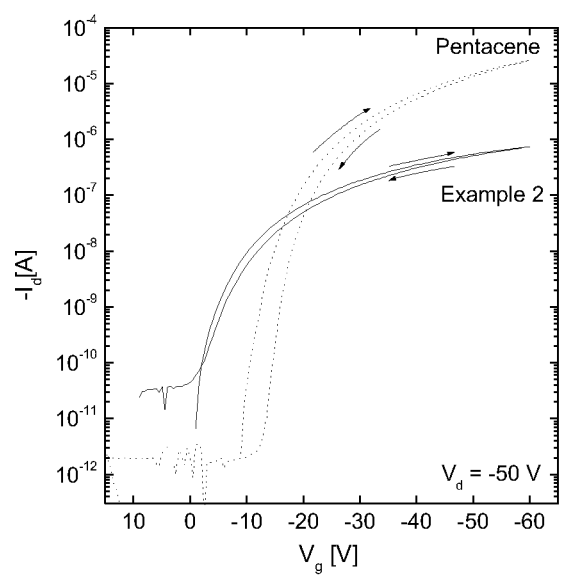
Fig. 4: Gate voltage/drain current sweeps of transistors using pentacene or the product of example 2 as semiconductor (example 8).

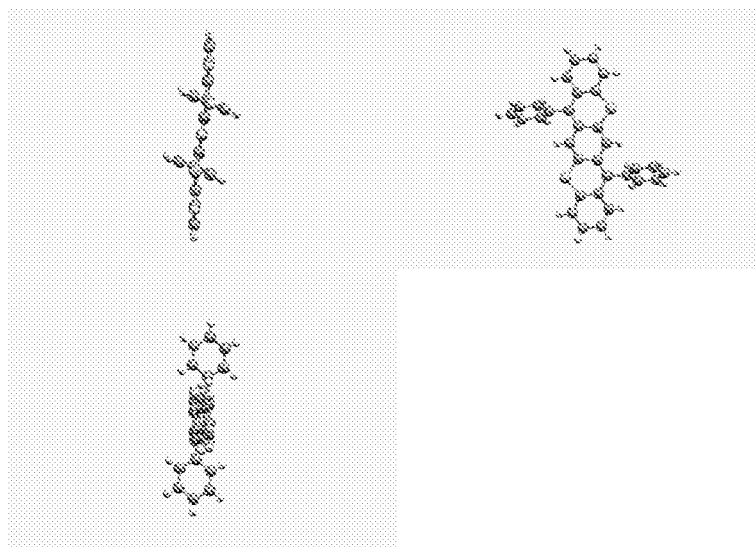
Fig. 5: Pictures of the molecule (product of example 13) calculated on basis of the x-ray diffraction analysis (views other than along crystallographic axes).

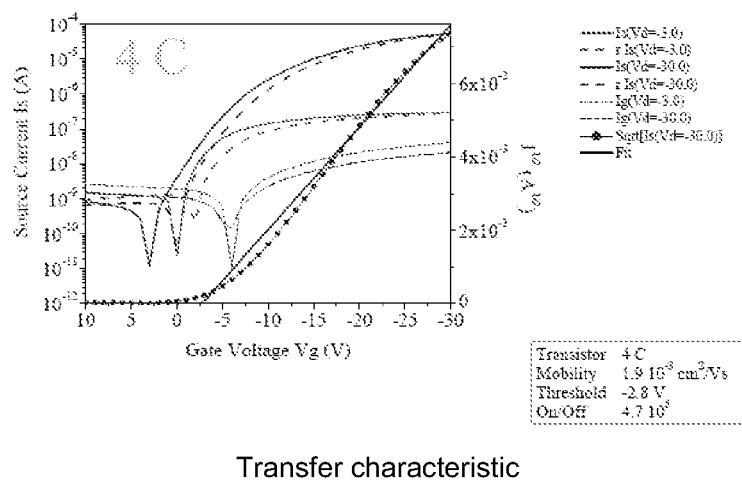
Transfer characteristic
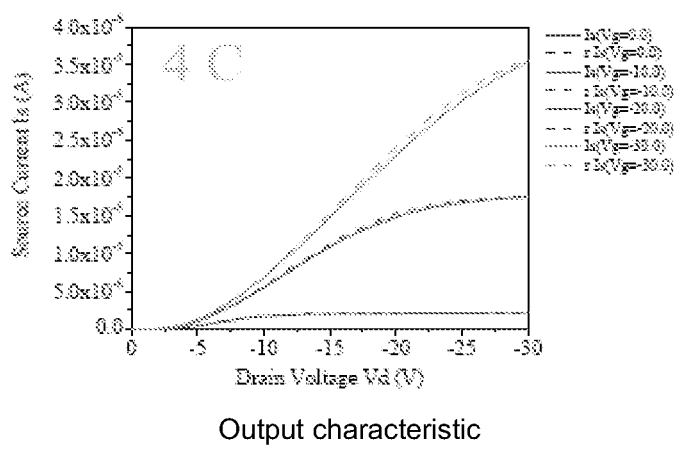
Output characteristic
Fig. 6: Transfer characteristics both on a linear scale and on a logarithmic scale (left; upper part) and output characteristics (lower part); transistor of example 14.

QUINOID SYSTEMS AS ORGANIC SEMICONDUCTORS

The present application pertains to a semiconductor device comprising a quinoid heteroacene as organic semiconductor, to a process for the preparation of said devices, to novel quinoid heteroacenes useful inter alia in said process, as well as to the corresponding use.

Organic semiconductor devices, e.g. organic diodes or especially organic field effect transistors (OFETs), promise a number of advantages over traditional inorganic semiconductors, such as low-cost manufacturing or compatibility with flexible substrates. Besides certain polymers (e.g. as described in Chem. Rev. 1997, 97, 173-205), a number of condensed aromatic compounds such as pentacene, certain condensed heteroaromatics or addition compounds thereof, have been found to exhibit useful semiconducting properties, inter alia characterized by high charge carrier (field effect) mobility, high on/off current ratio, low sub-threshold voltage. These advantageous features are, however, often compromised by factors like the necessity to use vapour deposition for the preparation of thin film devices, or lack of stability due to effects like recrystallization, phase transition, temperature or environmental influences like oxidizing conditions.

In order to improve the properties of organic semiconductors, structural modifications have been introduced into condensed aromatics, or addition compounds have been proposed (see, for example, JP-A-2000-231987; WO 02/068431; European patent application No. 05104009.5).

There is a need for organic semiconductors that can provide stable, reproducible electronic performance characteristics and that exhibit good charge-carrier mobilities while allowing for low-cost manufacturing.

It has now been found that certain, usually non-polymeric heteroacenes based on the quinoid 1,5-dihetero-anthracene as such surprisingly combine good semiconductor and applicative properties and thus may be used with advantage as organic semiconductors not only in diodes or organic light emitting diodes (OLEDs), but also in organic field effect transistors (OFETs), which are advantageously prepared as thin film transistors (OTFTs), and corresponding devices.

Thus, the present semiconductor may find uses in:
field effect transistors as components of integrated circuitry;
flexible circuit supports for display backplanes
large area devices such as large area image sensors and electronic paper (E-Paper)
integrated circuit logic elements for low end microelectronics, such as smart cards, radio frequency identification (RFID) tags, and memory/storage devices
photovoltaic devices (solar cells);
physical and chemical sensor devices.

The subject of the invention therefore generally pertains to a semiconductor device comprising a non-polymeric compound as organic semiconductor, characterized in that said compound is a quinoid diheteroacene of the formula I

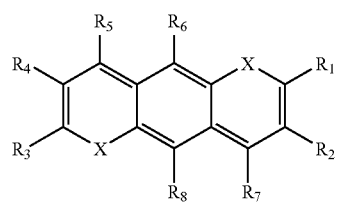

(I)

wherein X stands for O, S or NR, each of R, $R_1$, $R_2$, $R_3$, $R_4$, $R_5$, $R_6$, $R_7$, $R_8$, in general, being independently selected from hydrogen and an organic residue, while R is different from hydrogen, or 2 or more thereof together forming one or more annealed rings, which may be substituted or unsubstituted, carbocyclic or heterocyclic, aromatic, quinoid or aliphatic.

The compound of the formula I usually is of a molecular weight of less than 1200 g/mol and belongs to the symmetry group $C_s$ or especially $C_{2h}$.

Where residues are substituted, substituents usually bond to a carbon atom and are selected from $C_1$-$C_{22}$alkoxy, $C_1$-$C_{22}$alkyl, $C_4$-$C_{12}$cycloalkoxy, $C_3$-$C_{12}$cycloalkyl, OH, halogen, aryl such as phenyl and naphthyl; saturated carbons, especially in positions other than alpha to a conjugated double bond (in order to avoid tautomeric "rearomatization" of the quinoid system) also may be substituted by oxo (=O); adjacent substituents may be linked together, e.g. to form a lactone, anhydride or imide or carbocyclic ring. Preferred substituents are alkyl or alkoxy; of specific technical interest are those containing 4 or more, especially 5 or more carbon atoms (see below), or halogen. In preferred compounds, any substituent, if present, is a monovalent substituent (bonds with a single bond).

The semiconducting effect is achieved by the present quinoid ring systems without the need of further components such as compounds forming a complex with the present quinoid diheteroacene compounds of the formula I (e.g. metal or boron compounds); the present semiconductor device thus usually does not contain such a component combined with the present compounds in the same environment. The present compounds usually are not used in the form of an adduct with another chemical entity.

BRIEF DESCRIPTION OF THE DRAWINGS

FIG. 1: Drain current ($I_D$) at constant gate voltage ($V_G$); transistor of example 4.

FIG. 2: Transfer characteristics both on a linear scale and on a logarithmic scale (left) and output characteristics (right); transistor of example 5a.

FIG. 3: TFT transfer characteristics with and without substrate surface treatment (example 7).

FIG. 4: Gate voltage/drain current sweeps of transistors using pentacene or the product of example 2 as semiconductor (example 8).

FIG. 5: Pictures of the molecule (product of example 13) calculated on basis of the x-ray diffraction analysis (views other than along crystallographic axes).

FIG. 6: Transfer characteristics both on a linear scale and on a logarithmic scale (left; upper part) and output characteristics (lower part); transistor of example 14.

At least one of the semiconducting materials used in said device, especially in form of a thin layer or a multitude of thin layers, preferably is a compound of the formula I wherein R is selected from unsubstituted or substituted alkyl, unsubstituted or substituted alkenyl, unsubstituted or substituted alkynyl, unsubstituted or substituted aryl;

each of $R_1$, $R_2$, $R_3$, $R_4$, $R_5$, $R_6$, $R_7$, $R_8$ independently is selected from H, unsubstituted or substituted alkyl, unsubstituted or substituted alkenyl, unsubstituted or substituted alkynyl, unsubstituted or substituted aryl, halogen, substituted silyl, $XR_{12}$; or one or more of R, $R_1$, $R_2$, $R_3$, $R_4$, $R_5$, $R_6$, $R_7$, $R_8$, together with the carbon or nitrogen atoms they are bonding to, form a saturated or unsaturated, unsubstituted or substituted carbocyclic or heterocyclic annealed ring;

$R_{12}$ is unsubstituted or substituted alkyl, unsubstituted or substituted alkenyl, unsubstituted or substituted alkynyl, substituted silyl, acyl, unsubstituted or substituted aryl.

Preferred compounds of the formula I are those wherein each alkyl is selected from $C_1$-$C_{22}$alkyl, which may be interrupted by O, S, COO, OCNR10, OCOO, OCONR10, NR10CNR10, or NR10, where R10 is H, $C_1$-$C_{12}$alkyl, $C_3$-$C_{12}$cycloalkyl; each aryl is selected from $C_4$-$C_{18}$aromatic moieties, which may contain, as part of the ring structure, one or 2 heteroatoms selected from O, N and S, preferred aryl are selected from phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, benzothienyl;

annealed rings, where present, are formed by 2 or more of the residues $R_1$, $R_2$, $R_3$, $R_4$, $R_5$, $R_7$, and are aromatic carbocyclic or N-heterocyclic, substituted or unsubstituted 5- or 6-membered rings;

substituents, where present, bond to a carbon atom and are selected from $C_1$-$C_{22}$alkoxy, $C_1$-$C_{22}$alkyl, $C_4$-$C_{12}$cycloalkoxy, $C_3$-$C_{12}$cycloalkyl, OH, halogen, $Si(R11)_3$, phenyl, naphthyl; while saturated carbons also may be substituted by oxo (=O); 2 adjacent substituents may be linked together, e.g. to form a lactone, anhydride, imide or carbocyclic ring; especially, where the compound of the formula I conforms to the formula II

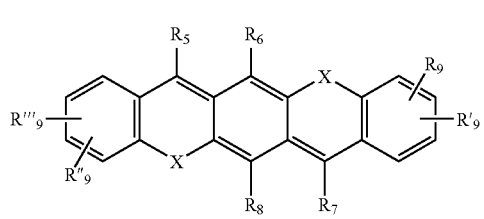

(II)

wherein
X stands for O, S or NR,
R is selected from unsubstituted or substituted $C_1$-$C_{18}$alkyl, unsubstituted or substituted $C_2$-$C_{18}$alkenyl, unsubstituted or substituted $C_2$-$C_{18}$alkynyl, unsubstituted or substituted $C_4$-$C_{18}$aryl;
each of $R_5$, $R_6$, $R_7$, $R_8$ independently is selected from H; unsubstituted or substituted $C_1$-$C_{22}$alkyl or $C_2$-$C_{22}$alkenyl, each of which may be interrupted by O, S, COO, OCNR10, OCOO, OCONR10, NR10CNR10, or NR10; substituted $C_2$-$C_{18}$alkynyl; unsubstituted or substituted $C_4$-$C_{18}$aryl; halogen; silyl$XR_{12}$;
$R_9$, $R'_9$, $R''_9$, $R'''_9$ independently are as defined for $R_5$, or adjacent $R_9$ and $R'_9$ and/or adjacent $R''_9$ and $R'''_9$, or $R_5$ and $R'''_9$, and/or $R_7$ and $R'_9$, together form an annealed ring;
R10 is H, $C_1$-$C_{12}$alkyl, $C_4$-$C_{12}$cycloalkyl; each silyl is SiH$(R11)_2$ or $Si(R11)_3$ with R11 being $C_1$-$C_{20}$-alkyl or -alkoxy;
$R_{12}$ is silyl, acyl, unsubstituted or substituted $C_1$-$C_{22}$alkyl, unsubstituted or substituted $C_4$-$C_{18}$aryl;
each aryl is selected from $C_4$-$C_{18}$aromatic moieties, which may contain, as part of the ring structure, one or 2 heteroatoms selected from O, N and S, preferred aryl are selected from phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, benzothienyl; annealed rings, where present, are aromatic carbocyclic or N-heterocyclic, substituted or unsubstituted 6-membered rings; and substituents, where present, bond to a carbon atom and are selected from $C_1$-$C_{22}$alkoxy, $C_1$-$C_{22}$alkyl, $C_4$-$C_{12}$cycloalkoxy, $C_4$-$C_{12}$cycloalkyl, OH, halogen, phenyl, naphthyl; while saturated carbons also may be substituted by oxo (=O); 2 adjacent substituents may be linked together, e.g. to form a lactone, anhydride, imide or carbocyclic ring.

In an example for the compound of the formula II,
X stands for O, S or NR,
R is selected from $C_1$-$C_{18}$alkyl, or unsubstituted or substituted phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, benzothienyl;
each of $R_5$, $R_6$, $R_7$, $R_8$ independently is selected from H; unsubstituted or substituted $C_1$-$C_{18}$alkyl or $C_1$-$C_{18}$alkoxy, each of which may be interrupted by O, S, or NR10; substituted ethynyl; unsubstituted or substituted phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, benzothienyl; halogen; $Si(R11)_3$;
$R_9$, $R'_9$, $R''_9$, $R'''_9$ independently are as defined for $R_5$, or adjacent $R_9$ and $R'_9$ and/or adjacent $R''_9$ and $R'''_9$ together form an annealed ring; or $R_5$ as unsubstituted or substituted phenyl is linked to $R'''_9$, and/or $R_7$ as unsubstituted or substituted phenyl is linked to $R'_9$, forming a 6-membered ring structure with $R'''_9$ and/or $R'_9$ being X or $CH_2$;
R10 is H, $C_1$-$C_{12}$alkyl, $C_4$-$C_{12}$cycloalkyl;
R11 is methyl, ethyl, propyl, methoxy, ethoxy, propoxy;
annealed rings, where present, are aromatic carbocyclic or N-heterocyclic, substituted or unsubstituted 5- or 6-membered rings; and substituents, where present, bond to a carbon atom and are selected from $C_1$-$C_{18}$alkoxy, $C_1$-$C_{18}$alkyl, $C_4$-$C_{12}$cycloalkoxy, $C_4$-$C_{12}$cycloalkyl, OH, halogen, phenyl, naphthyl; while saturated carbons also may be substituted by oxo (=O); 2 adjacent substituents may be linked together, e.g. to form a lactone, anhydride, imide or carbocyclic ring; preferably, X is O;
each of $R_5$, $R_6$, $R_7$, $R_8$ independently is selected from H; unsubstituted or substituted $C_1$-$C_{18}$alkyl or $C_1$-$C_{18}$alkoxy; substituted ethynyl; unsubstituted or substituted phenyl, naphthyl, pyridyl, chinolyl; halogen; $Si(R_{11})_3$;
$R_9$, $R'_9$, $R''_9$, $R'''_9$ independently are as defined for $R_5$, or adjacent $R_9$ and $R'_9$ and/or adjacent $R''_9$ and $R'''_9$, together with the connecting carbon atoms, form an annealed phenyl, naphthyl or pyridyl ring; or $R_5$ as unsubstituted or substituted phenyl is linked to $R'''_9$, and/or $R_7$ as unsubstituted or substituted phenyl is linked to $R'_9$, forming a 6-membered ring structure with $R'''_9$ and/or $R'_9$ being X;
R11 is methyl, ethyl, propyl, methoxy, ethoxy, propoxy; and substituents, where present, bond to a carbon atom and are selected from $C_1$-$C_{18}$alkoxy, $C_1$-$C_{18}$alkyl, cyclohexyloxy, cyclopentyloxy, cyclohexyl, cyclopentyl, halogen, phenyl, naphthyl;
while saturated carbons also may be substituted by oxo (=O).

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH=CH—]$_n$ or —[CH=C(CH$_3$)—]$_n$, where n may be, for example, from the range 2-50. Preferred alkyl contains 1-22 carbon atoms;

preferred alkenyl and alkinyl each contains 2-22 carbon atoms, especially 3-22 carbon atoms.

Any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, $C_1$-$C_{12}$alkyl, $C_3$-$C_{12}$cycloalkyl, phenyl. They can be interrupted by one or more of these spacer groups, one group in each case being inserted, in general, into one carbon-carbon bond, with hetero-hetero bonds, for example O—O, S—S, NH—NH, etc., not occurring; if the interrupted alkyl is additionally substituted, the substituents are generally not $\alpha$X to the heteroatom. If two or more interrupting groups of the type —O—, —NR10—, —S— occur in one radical, they often are identical.

The term alkyl, whereever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

The term alkenyl, whereever used, thus mainly embraces especially uninterrupted and, where appropriate, substituted $C_2$-$C_{22}$alkyl such as vinyl, allyl, etc.

Where aryl (e.g. in $C_1$-$C_{14}$-aryl) is used, this preferably comprises monocyclic rings or polycyclic ring systems with the highest possible number of double bonds, such as preferably phenyl, naphthyl, anthrachinyl, anthracenyl or fluorenyl. The term aryl mainly embraces $C_1$-$C_{18}$aromatic moieties, which may be heterocyclic rings (also denoted as heteroaryl) containing, as part of the ring structure, one or more heteroatoms mainly selected from O, N and S; hydrocarbon aryl examples mainly are $C_6$-$C_{18}$ including phenyl, naphthyl, anthrachinyl, anthracenyl, fluorenyl; examples for heterocyclics ($C_1$-$C_{18}$) include those of the following table:

| ring structure | name | monovalent residue |
|---|---|---|
|  | pyridine | pyridyl |
|  | pyrimidine | pyrimidyl |
|  | pyridazine | pyridazyl |
|  | pyrazine | pyrazyl |
|  | thiophene | thienyl |
|  | benzothiophene | benzothienyl |
|  | pyrrol | pyrryl |
|  | furane | furyl |
|  | benzofurane | benzofuryl, |
|  | indole | indyl |
|  | carbazole | carbazolyl |
|  | benzotriazole | benzotriazolyl |
|  | tetrazole | tetrazolyl |
|  | thiazole | thiazolyl |
|  | | thienothienyl |
|  | | dithiaindacenyl |
|  | | chinolyl |

| ring structure | name | monovalent residue |
|---|---|---|
| 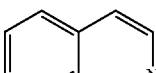 | | isochinolyl |
| 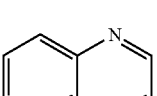 | | chinoxalyl |
| 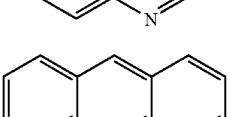 | | acridyl | as well as azanaphthyl, phenanthryl, triazinyl, tetrahydronaphthyl, thienyl, pyrazolyl, imidazolyl,

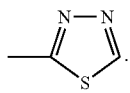

Preferred are $C_4$-$C_{18}$aryl, e.g. selected from phenyl, naphthyl, pyridyl, tetrahydronaphthyl, furyl, thienyl, pyrryl, chinolyl, isochinolyl, anthrachinyl, anthracenyl, phenanthryl, pyrenyl, benzothiazolyl, benzoisothiazolyl, benzothienyl; most preferred is phenyl, naphthyl, thienyl.

Acyl stands for an aliphatic or aromatic residue of an organic acid —CO—R', usually of 1 to 30 carbon atoms, wherein R' embraces aryl, alkyl, alkenyl, alkynyl, cycloalkyl, each of which may be substituted or unsubstituted and/or interrupted as described elsewhere inter alia for alkyl residues, or R' may be H (i.e. COR' being formyl). Preferences consequently are as described for aryl, alkyl etc.; more preferred acyl residues are substituted or unsubstituted benzoyl, substituted or unsubstituted $C_1$-$C_{17}$alkanoyl or alkenoyl such as acetyl or propionyl or butanoyl or pentanoyl or hexanoyl, substituted or unsubstituted $C_5$-$C_{12}$cycloalkylcarbonyl such as cyclohexylcarbonyl.

Halogen denotes I, Br, Cl, F, preferably Cl, F, especially F. Also of specific technical interest are perhalogenated residues such as perfluoroalkyl, e.g. of 1 to 12 carbon atoms such as $CF_3$.

Substituted silyl is preferably Si substituted by two or preferably three moieties selected from unsubstituted or substituted hydrocarbyl or hydrocarbyloxy (wherein the substituents are preferably other than substituted silyl), as defined above, or by unsubstituted or substituted heteroaryl. In case that Si carries only two substituents, the silyl group is of the type —SiH($R_2$) with $R_2$ preferably being hydrocarbyl or hydrocarbyloxy. More preferred are three $C_1$-$C_{20}$-alkyl or -alkoxy substituents, i.e. substituted silyl then is Si(R11)$_3$ with R11 being $C_1$-$C_{20}$-alkyl or -alkoxy, especially three $C_1$-$C_8$-alkyl substitutents, such as methyl, ethyl, isopropyl, t-butyl or isobutyl.

In each case where mentioned, "unsaturated" preferably means having the maximum possible number of conjugated double bonds.

Preferred alkynyl residues are substituted ethynyl, i.e. ethynyl (—C≡C—H) wherein the hydrogen is substituted by one of the substituents mentioned above, where general expression can preferably be replaced by the more detailed definitions given below.

Cycloalkyl such as $C_3$-$C_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are $C_3$-$C_6$cycloalkyl as well as cyclododecyl, especially cyclohexyl.

As substituted ethynyl, ethynyl substituted by unsubstituted or substituted $C_1$-$C_{20}$-alkyl (which can be primary, secondary or tertiary), unsubstituted or substituted phenyl, unsubstituted or substituted (e.g. 1- or 2-) naphthyl, unsubstituted or substituted (e.g. 1-, 2- or 9-) anthracenyl, an unsubstituted or substituted heteraryl moiety or a substituted silyl moiety selected from those given in the following table—the respective moiety can be bound via any ring atom appropriate, preferably by one of those marked with an asterisk, to the ethynyl moiety instead of a hydrogen in unsubstituted ethynyl—are especially preferred:

Table of some preferred substitutents for substituted ethynyl (which can be substituted or preferably unsubstituted as described above):

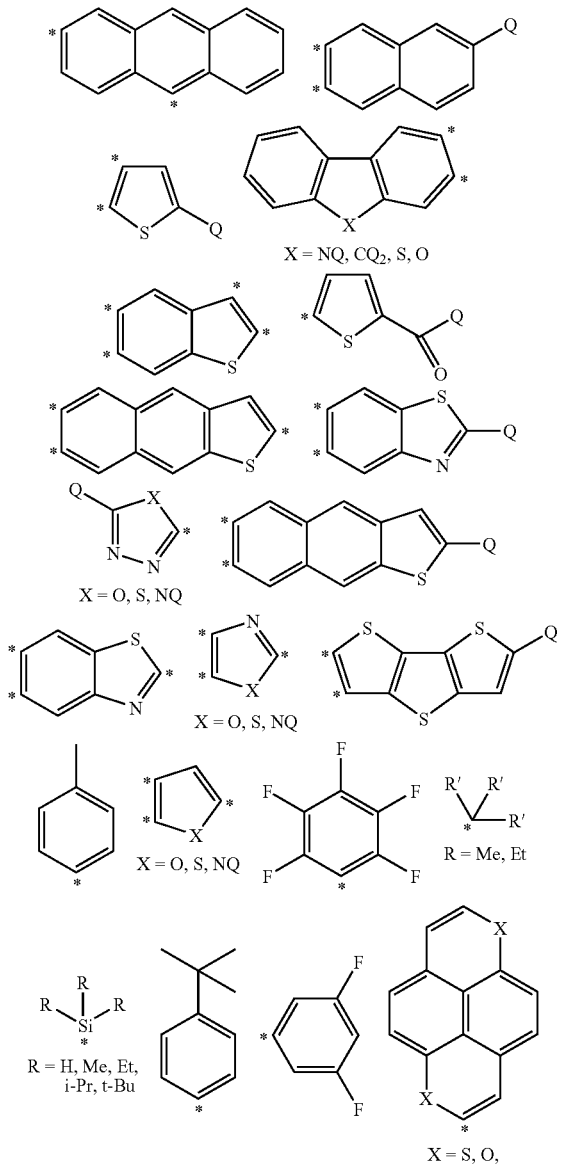

-continued

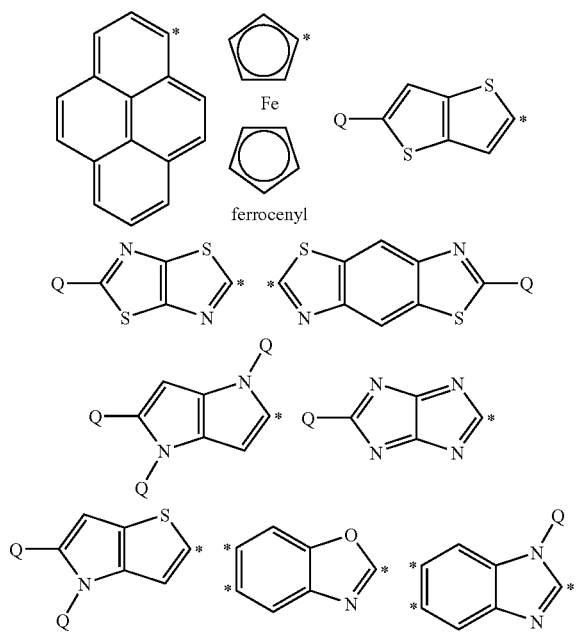

In the table, Q is as defined above for a compound of the formula I, especially selected from hydrogen, aryl, especially C$_6$-C$_{14}$-aryl, aryl-alkyl, especially phenyl- or naphthyl-C$_1$-C$_{20}$-alkyl, heteroaryl, especially with up to 14 ring atoms, and alkyl, especially C$_1$-C$_{20}$-alkyl.

Generally, binders and/or dopants or the like may be present in a semiconductor device according to the present invention, however, preferably in an amount of less than 5%, e.g. in thin films in thin film transistors which are described in more detail below. Possible binders are, e.g., described in WO 2005/055248 which is incorporated by reference here by reference concerning the binders and compositions where the polyacenes of formula A therein are replaced with compounds of the formula I, preferably IA and more preferably IB or ICas described in the present text.

The alkyl, alkenyl or alkynyl moieties mentioned herein can be linear or branched one or more times (if the number of carbon atoms therein allows so). Preferably, they have up to 20 carbon atoms, in another preferred embodiment up to 8 carbon atoms.

Certain compounds of the invention are well soluble in organic solvents and are therefore better candidates for economical solution processing methods of deposition. Still, the present structures allow for an efficient stacking and crystallization (packing with good π-π-interaction), thus providing high intermolecular flow of charge carriers.

The compounds of the invention show high stability against thermal and/or oxidative degradation; they are also useful as charge transport materials, dyes, fluorescent dyes or as infrared absorbing materials.

Preparation

In general, compounds of the formula I may be obtained according to, or in analogy to, methods known in the art, such as those described by Liebermann et al., Liebigs Ann. Chem. (1934), 38.

For example, preparation of a preferred compound of the formula I may be conveniently be effected according to the scheme:

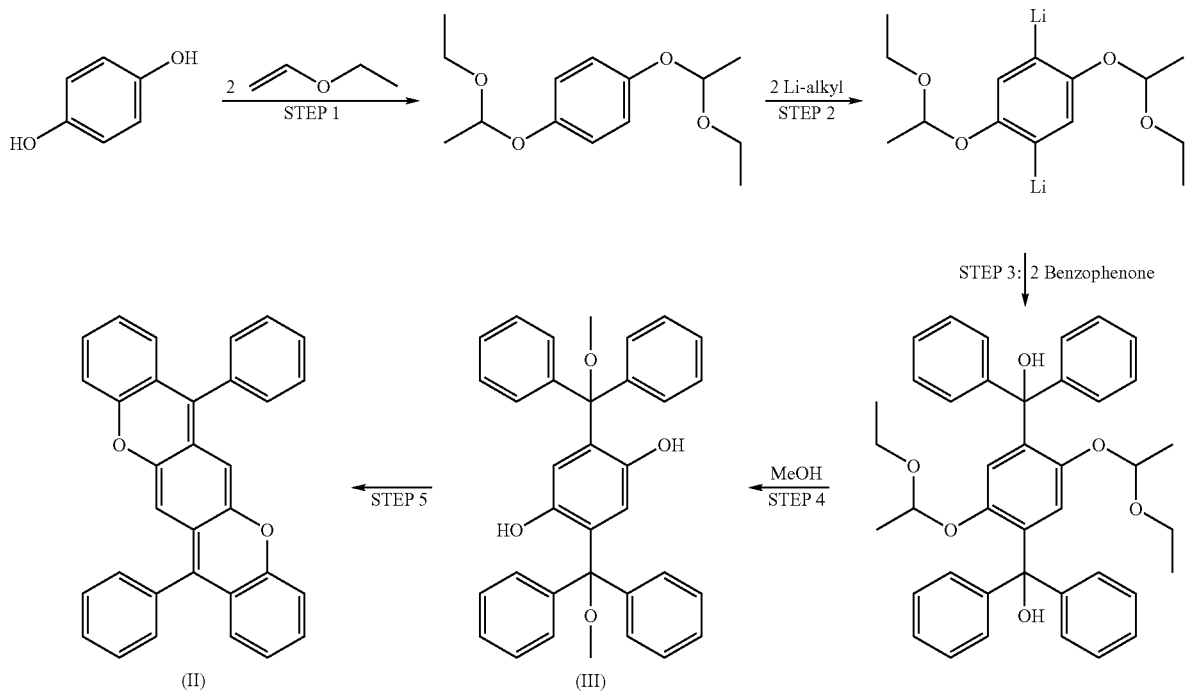

Reactions may be carried out in a conventional manner, e.g. using inert solvents, equipment and temperatures as required. Steps 1 and 4 therein are advantageously carried out with acid catalysis (e.g. HCl); of course, other suitable protection groups than ethyl vinyl ether may be used as well (e.g. dihydropyrane). The reaction with Li-alkyl (such as n-butyllithium) in step 2 may conveniently run at moderate temperatures (e.g. using an ether solvent such as diethyl ether at room temperature (15-25° C.), and optionally with a base as catalyst (e.g. tertiary amines such as tetramethylethylenediamine TMEDA). The ring closure in step 5 may be effected with acid catalysis and/or heating, e.g. using sulfuric acid as catalyst with heating (e.g. 200° C.), for example in an organic solvent of low volatility such as nitrobenzene.

Alternative structures, e.g. of formula I or II with X being S or NR, or different substituents especially for alternative annealed rings $R_1/R_2$ and $R_3/R_4$, and alternative residues $R_5$ and $R_7$, may be obtained using suitable educts, e.g. after replacing hydroquinone used in the above scheme by the corresponding dithio compound or by 1,4-diaminobenzene or by corresponding 2,5-disubstituted compounds. The benzophenone reagent in step 3 may be replaced by another suitable carbonyl compound such as xanthone, thioxanthone.

Another procedure starts from a suitable derivative of 2,5-dihydroxy-terephthalic acid (e.g. an ester thereof), which is conveniently converted into the corresponding quinone. Reacting said quinone with an XH-substituted aryl yields an intermediate of the structure aryl-X-quinone-X-aryl, whose carboxy (ester) moieties may undergo a ring closure reaction (e.g. with acid catalysis/heating); the remaining keto groups are easily reduced to form the present product, e.g. of formula II, which may be further derivatized; an example is given in the following scheme:

wherein L stands for a leaving group (e.g. halogen), Hal is halogen,
R independently is alkyl or substituted alkyl, e.g. conforming to the definitions given for $R_5$-$R_9$, Ar stands for an aryl moiety, e.g. phenyl, substituted phenyl or annealed phenyl such as naphthyl; other symbols are as defined above.

Similarly, the present compounds may also be prepared in analogy to synthesis methods given by Freund et al., Angew. Chem. Int. Ed. Engl. 33, 2424 (1994), starting from a suitable 1,4-diketo-benzene reacted with 2 Ar—X—H and following ring closure. The resulting product may conveniently be converted into the quinoid form by dehydrogenation following methods known in the art, e.g. by heating in presence of sulfur or selen in presence of a high boiling solvent such as pyridine, quinoline etc. and/or applying pressure; or by catalytic dehydrogenation e.g. using Ir or Pt on support; or dehydrogenation using quinones such as chloranil or DDQ (dichloro-dicyanobenzoquinone), or using an hydride acceptor such as tritylium perchlorate or tritylium fluoroacetate.

The synthesis especially of compounds of the formula II may be carried out in analogy to the methods given by Liebermann et al., Liebigs Ann. Chem. 513, 156 (1934).

Compounds of the formula I as well as preferred compounds of formula II or III as defined above may be further derivatized using methods known in the art such as etherification, thioetherification or amination etc. Compounds of the present formula I or II having suitable functional groups, e.g.

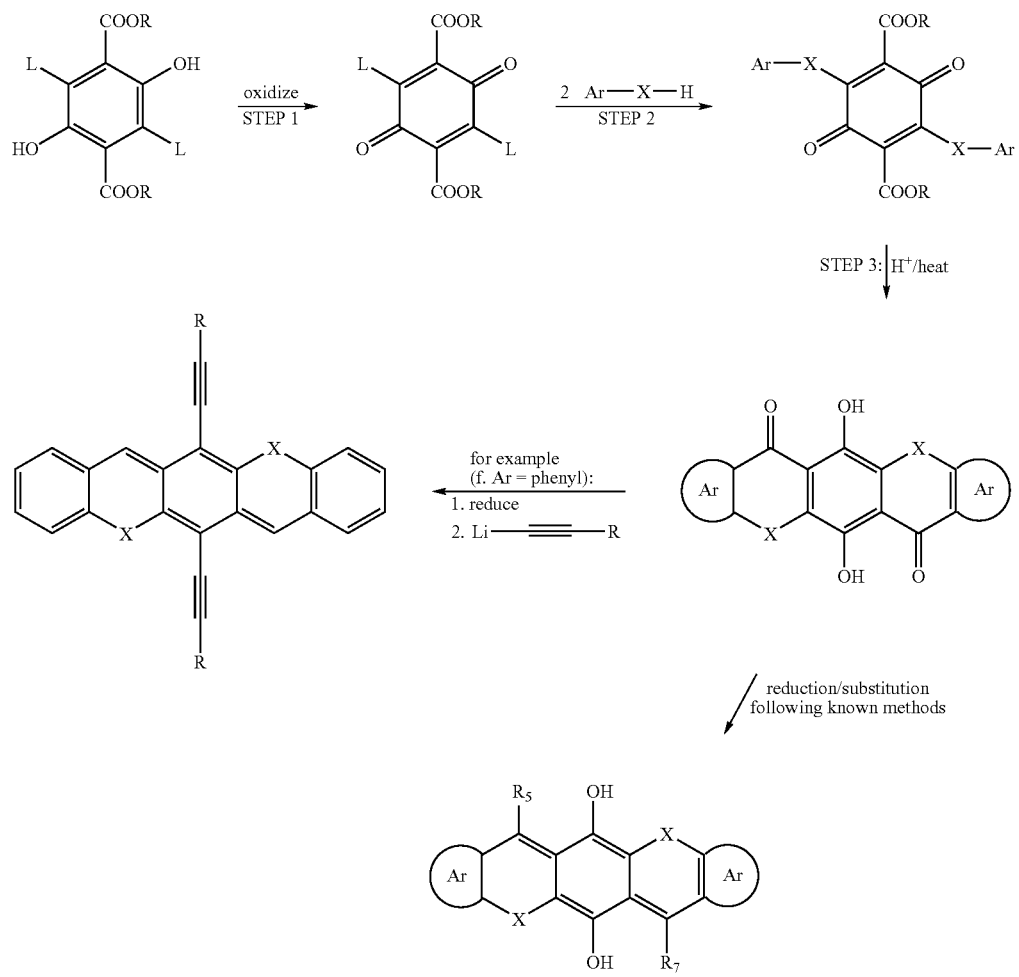

bromo, boronic acid, vinyl etc., especially when attached to the aryl core, may also be converted into a polymeric structure according to methods known in the art. Polymers of the present compounds generally have comparably advantageous properties as the compounds of formula I or II. The invention therefore further pertains to a The precursor of formula III

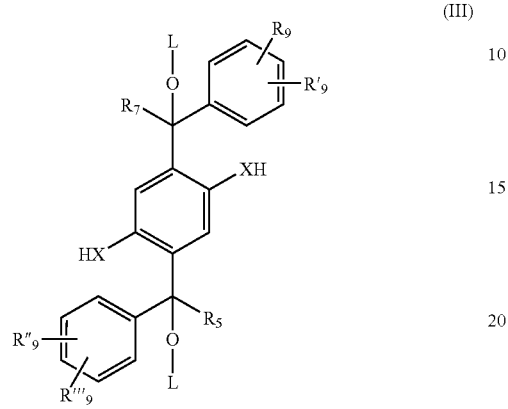

(III)

may also be applied to a substrate by conventional techniques such as dipping, printing, stamping etc., especially as a thin film. The semiconducting layer of compounds of the formula I or II thus may be prepared by suitable thermal treatment of a previously prepared layer of the precursor of the formula III (latent semiconductor).

Therefore, it is a further object of the present invention to prepare a thin semiconducting layer of a compound of the formula I or II by solid state conversion of a thin film of the precursor of formula III. It is further another object of the present invention to provide films of a compound of the formula I or II for the fabrication of TFT devices that are prepared by a low to moderate temperature conversion of a precursor thereof to the semiconducting compound at about 60° C. to about 300° C.

It is another object of the present invention to prepare thin films of a soluble precursor of formula III, using a suitable solvent, e.g. selected from organic solvents.

A film layer of the compound of the present formulae I or II, or of a precursor of the formula III, may be formed by applying a solution of the compound onto a substrate and thereafter removing the solvent, or may be formed following methods known in the art such as vacuum deposition.

It is yet another object of the present invention to use a thin film of a compound of the formula I or II in a diode or transistor, e.g. a thin film transistor, as a p-type or n-type semiconductor channel.

Novel Compounds

Some of the present semiconducting compounds are novel. The invention therefore also pertains to a compound of the formula II' or IV

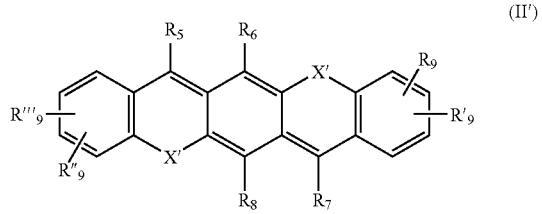

(II')

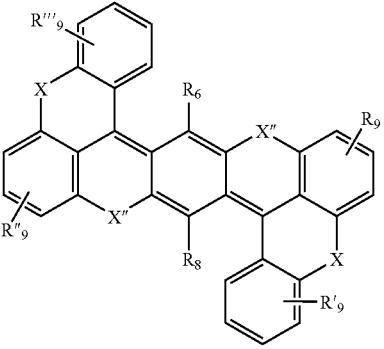

(IV)

wherein
X' stands for S or NR,
X and X" stand for O, S or NR,
and all other symbols and preferred meanings are as defined above for formula II.

The compound of the formula IV often conforms to the formula:

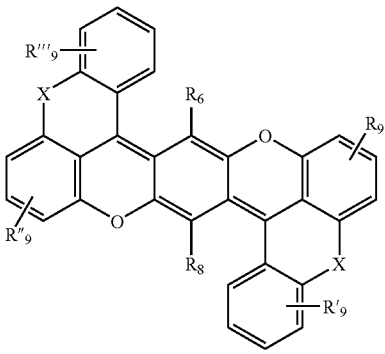

(IV')

Semiconductor Devices

The compounds of the invention can be used as the semiconductor layer in semiconductor devices. There are numerous types of semiconductor devices. Common to all is the presence of one or more semiconductor materials. Semiconductor devices have been described, for example, by S. M. Sze in Physics of Semiconductor Devices, 2.nd edition, John Wiley and Sons, New York (1981). Such devices include rectifiers, transistors (of which there are many types, including p-n-p, n-p-n, and thin-film transistors), light emitting semiconductor devices (for example, organic light emitting diodes), photoconductors, current limiters, thermistors, p-n junctions, field-effect diodes, Schottky diodes, and so forth. In each semiconductor device, the semiconductor material is combined with one or more metals or insulators to form the device. Semiconductor devices can be prepared or manufactured by known methods such as, for example, those described by Peter Van Zant in Microchip Fabrication, Fourth Edition, McGraw-Hill, New York (2000).

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2.sup.nd edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly (3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric. Organic polymers such as poly (arylene ethers), bisbenzocyclobutenes, fluorinated polyimides, polytetrafluoroethylene, parylenes, polyquinolines etc are also useful for the gate dielectric.

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or ink jet printing. The patterning of these electrodes can be accomplished by known methods such as shadow masking, additive photolithography, subtractive photolithography, printing, microcontact printing, and pattern coating.

The present invention further provides a thin film transistor device comprising
a plurality of electrically conducting gate electrodes disposed on a substrate;
a gate insulator layer disposed on said electrically conducting gate electrodes;
an organic semiconductor layer disposed on said insulator layer substantially overlapping said gate electrodes; and
a plurality of sets of electrically conductive source and drain electrodes disposed on said organic semiconductor layer such that each of said sets is in alignment with each of said gate electrodes;
wherein said organic semiconductor layer is a quinoid 1,5-diheteroanthracene compound of the formula I or II.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a layer of a quinoid 1,5-diheteroanthracene compound of the formula I or II or a precursor thereof of formula III on said insulator layer such that said layer substantially overlaps said gate electrodes;
depositing a plurality of sets of electrically conductive source and drain electrodes on said layer such that each of said sets is in alignment with each of said gate electrodes; and, in case that a precursor of formula III has been used, heating to convert said precursor to a quinoid 1,5-diheteroanthracene compound of the formula I or II, thereby producing the thin film transistor device.

Any suitable substrate can be used to prepare the thin films of the quinoid 1,5-diheteroanthracene compounds of the present invention as well as the thin films of the precursor thereof. Preferably, the substrate used to prepare the above thin films is a metal, silicon, plastic, paper, coated paper, fabric, glass or coated glass.

Alternatively, a TFT is fabricated by, for example, by solution deposition of a quinoid 1,5-diheteroanthracene or its precursor on a highly doped silicon substrate covered with a thermally grown oxide layer followed by vacuum deposition and patterning of source and drain electrodes. In the last step, the device is optionally heated so that the precursor is converted to a quinoid 1,5-diheteroanthracene film.

In yet another approach, a TFT is fabricated by deposition of source and drain electrodes on a highly doped silicon substrate covered with a thermally grown oxide and then solution deposition of the quinoid 1,5-diheteroanthracene or its precursor to form a thin film, and finally heating the device in case that the precursor has been used to convert it to quinoid 1,5-diheteroanthracene.

The gate electrode could also be a patterned metal gate electrode on a substrate or a conducting material such as, a conducting polymer, which is then coated with an insulator applied either by solution coating or by vacuum deposition on the patterned gate electrodes. The insulator can be a material, such as, an oxide, nitride, or it can be a material selected from the family of ferroelectric insulators, including but not limited to $PbZr_xTi_{1-x}O_3$ (PZT), $Bi_4Ti_3O_{12}$, $BaMgF_4$, $Ba(Zr_{1-x}Ti_x)O_3$ (BZT), or it can be an organic polymeric insulator.

Any suitable solvent can be used to dissolve the precursor or the present quinoid 1,5-diheteroanthracene compound, provided it is inert, can dissolve at least some of material and can be removed from the substrate by conventional drying means (e.g. application of heat, reduced pressure, airflow etc.). Suitable organic solvent for processing the semiconductors of the invention include, but are not limited to, aromatic or aliphatic hydrocarbons, halogenated such as chlorinated hydrocarbons, esters, ethers amides, such as chloroform, tetrachloroethane, tetrahydrofuran, toluene, ethyl acetate, methyl ethyl ketone, dimethyl formamide, dichlorobenzene, propylene glycol monomethyl ether acetate (PGMEA) and mixtures thereof. The solution is then applied by a method, such as, spin-coating, dip-coating, screen printing, microcontact printing, doctor blading or other solution application techniques known in the art on the substrate to obtain thin films of the semiconducting material or its precursor.

Preferably, the thickness of the organic semiconductor layer is in the range of from about 5 to about 200 nm, especially the thickness is in the range of from about 10 to about 30 nm.

The quinoid 1,5-diheteroanthracene compounds of the invention can be used alone or in combination as the organic semiconductor layer of the semiconductor device. The layer can be provided by any useful means, such as, for example, vapor deposition and printing techniques. Some of the compounds of the invention (for example, those bearing sufficiently large alkyl groups such as two dodecyl, nonyl, or hexyl substituents, especially unbranched ones which are uninterrupted, or branched or unbranched interrupted groups such as alkyls branched in α-position to the heterofunction) are sufficiently soluble in organic solvents and can be solution deposited (for example, by spin coating, dip coating, ink jet printing, casting, or other known techniques).

In case of chiral side chains, the selection of diastereomerically pure molecules for the preparation of the semiconducting layer is preferred.

The quinoid 1,5-diheteroanthracene compounds of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

The following examples are for illustrative purposes only and are not to be construed to limit the instant invention in any manner whatsoever. Room temperature/ambient temperature depicts a temperature in the range 20-25° C.; over night denotes a time period in the range 12-16 hours. Percentages are by weight unless otherwise indicated.

Abbreviations used in the examples or elsewhere:

M concentration in moles per liter n-BuLi n-butyllithium

OTS octadecyltrichlorosilane

MS mass spectrometry

μ non-contact corrected saturation field-effect mobility [cm$^2$/Vs]

$V_{on}$ onset voltage $V_t$ threshold voltage $I_{off}$ off-current [A]

$I_{on}/I_{off}$ on-off current ratio

EXAMPLE 1

Preparation of 2,5-Bis-(hydroxy-diphenyl-methyl)-benzene-1,4-diol

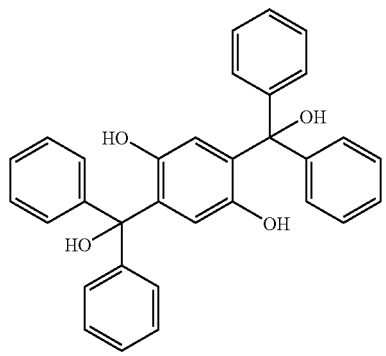 [SMILES: Oc1cc(C(O)(c2ccccc2)c2ccccc2)c(O)cc1C(O)(c1ccccc1)c1ccccc1]

A 250 ml Schlenk flask is charged with 1,4-bis-(1-ethoxy-ethoxy)-benzene (10.16 g, 40 mmol) and flushed with nitrogen. Then diethyl ether (50 ml), n-BuLi (29.6 ml of a 2.7 N solution in heptane, 80 mmol) and N,N,N',N'-tetramethyl ethylenediamine (9.3 g, 80 mmol) are added. There is a small increase of the temperature, and the mixture becomes cloudy. After stirring over night the mixture has turned into a thick slurry to which a solution of benzophenone (14.58 g, 80 mmol) in diethyl ether (in total 50 ml) is added dropwise. In a slightly exothermic reaction a greenish blue solution is formed, which is stirred for another 45 minutes. Then the solvents are removed on the rotavapor, and the residue treated with a mixture of ether (ca. 150 ml) and an ammonium chloride solution (ca. 100 ml of a 10% solution). The clear organic layer is separated and the solvent is removed on the rotavapor to leave 26.3 g of an oil. This is re-dissolved in methanol (ca. 200 ml) and ca. 0.5 ml of 36% HCl is added to the mixture. After standing over night, a colourless solid has formed, which is filtered off and dried (10.55 g).

EXAMPLE 2

Preparation of 7,14-Diphenyl-chromeno[2,3-b]xanthene

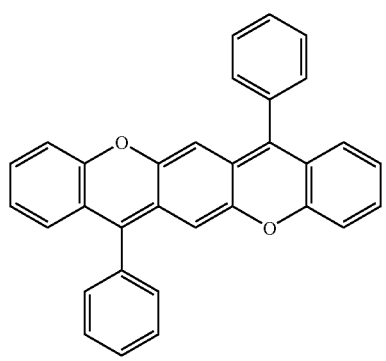 [SMILES: c1ccc(C2=c3cc4c(cc3Oc3ccccc32)=C(c2ccccc2)c2ccccc2O4)cc1]

A flask is charged with 2,5-bis-(hydroxy-diphenyl-methyl)-benzene-1,4-diol (Example 1) (9.5 g) and nitrobenzene (50 g). The obtained suspension is heated at reflux for ca. 45 minutes, and then allowed to cool over night. The formed crystals are filtered off, washed several times with ethanol and dried at $10^{-3}$ mbar/190° C. for two hours (some sublimation takes place) to give 4.47 g of greenish red crystals, mp.=419° C. (DSC). Elementary analysis: $C_{calcd.}$ 88.05%, $C_{found}$ 87.62% and 87.78%; $H_{calcd.}$ 4.62%, $H_{found}$ 4.29% and 4.65%. The proposed structure is confirmed by an X-ray crystal structure, monoclinic, space group C2/c, a=18.961(5), b=6.058(2), c=20.229 (5); alpha=90.00, beta=116.351(9), gamma=90.00; Z=4.

EXAMPLE 3 a) 2,5-Bis-[bis-(4-chloro-phenyl)-methoxy-methyl]-benzene-1,4-diol

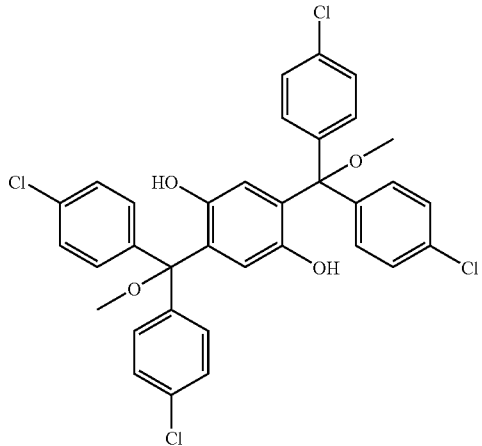 [SMILES: COC(c1ccc(Cl)cc1)(c1ccc(Cl)cc1)c1cc(O)c(C(OC)(c2ccc(Cl)cc2)c2ccc(Cl)cc2)cc1O]

A 250 ml Schlenk flask is charged with 1,4-bis-(1-ethoxy-ethoxy)-benzene (10.16 g, 40 mmol) and flushed with nitrogen. Then diethyl ether (50 ml), n-BuLi (29.6 ml of a 2.7 N solution in heptane, 80 mmol) and N,N,N',N'-tetramethyl ethylenediamine (9.3 g, 80 mmol) are added. The mixture is stirred over night, and then a solution of 4,4'-dichlorobenzophenone (20.1 g, 80 mmol) in warm (60° C.) THF (50 ml) is added dropwise within 5 minutes. There is a slight exotherm, and after 20 minutes of stirring a light brown solution is obtained. This solution is poured into water (ca. 200 ml) and after mixing the aqueous layer is removed. Then diethyl ether (ca. 100 ml) is added, and the organic layer washed again with water (twice ca. 200 ml) and 10% ammonium chloride solution (ca. 100 ml). Then the solvent is removed on the rotavapor, and the residue re-dissolved in methanol (ca. 200 ml). A colourless solid formed, which dissolves after the addition of 32% HCl (2 ml), forming a deep brownred solution which is left standing for two hours at ambient temperature. The solvent is removed on the rotavapor and the residue again dissolved in methanol (200 ml) and 32% HCl (2 ml) is added. The mixture is left standing for another hour at ambient temperature and the solvent is removed on the rotavapor. The residue is treated with little methanol and the solid is filtered off, washed with little chilled methanol and dried to leave 14.6 g (56.9%) of the product as colourless crystals.

$^1$H-NMR (300 MHz, CDCl$_3$) δ 2.87 (s, 3H, OCH$_3$); 7.01 (s, 1H, CH); 7.34 (s, 8H, Ar CH); 8.66 (s, 1H, OH). $^{13}$C-NMR (75 MHz, CDCl$_3$) δ 52.28 (OCH$_3$); 84.86 (COMe); 116.54 (Ar CH); 128.05 (Ar CH); 129.30 (q C); 130.80 (Ar CH); 132.17 (q C); 141.70 (Ar CCl); 146.99 (Ar COH).

b) 3,10-Dichloro-7,14-bis-(4-chloro-phenyl)-chromeno[2,3-b]xanthene

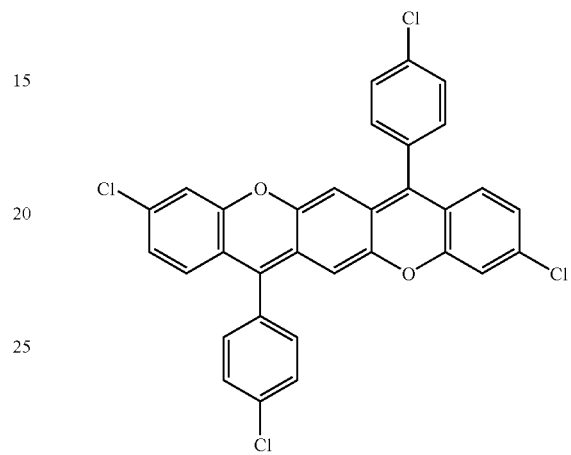

A solution of the product from example a (2,5-bis-[bis-(4-chloro-phenyl)-methoxy-methyl]-benzene-1,4-diol, 1.0 g, 1.56 mmol) is dissolved in nitrobenzene (5 ml) and the solution heated at reflux. The initially colourless solution turns red and later deeply violet. After one hour at reflux, the mixture is allowed to cool and then filtered. The product (violet needles) is washed with plenty of methanol and dried. MS shows the correct mass and isotopic pattern of four chlorines.

EXAMPLE 4

Single Crystal Field-Effect Transistor

Single crystals are grown by physical vapour transport in a horizontal oven with in inert carrier gas (argon). A temperature gradient is present, resulting in evaporation of 7,14-diphenyl-chromeno[2,3-b]xanthene of example 2 at 295° C. and crystallisation between 270° C. and 240° C. Crystals are obtained as thin red-brown plates.

A crystal is placed on a pre-fabricated substrate, consisting of a heavily doped silicon wafer, 300 nm of thermally grown SiO$_2$ and 18 nm thick gold contacts deposited through a shadow mask. The SiO$_2$ surface is treated with octadecyl-trichlorosilane (OTS) by exposing it in vacuum to OTS vapour at 120° C. for 1 hour.

The FET is characterized using an HP 4155A® semiconductor parameter analyzer by sweeping the gate voltage $V_G$ and keeping the drain voltage $V_D$ constant and vice versa (see FIG. 1). Both output and transfer characteristics contain only a small hysteresis.

Data for this sample are: $\mu_{sat}=\mu_{lin}=0.16$ cm$^2$/Vs, $V_t=1$ V, S=1.5 V/dec and $I_{on}/I_{off}=10^5$. After 10 weeks stored under helium atmosphere, the linear and saturated mobilities and the $I_{on}/I_{off}$ remain unchanged.

EXAMPLE 5

Thin Film Transistor

A) Purification and Thin Film Preparation

Compound of example 2 is purified in a 3 zone-oven by train-sublimation using argon as a carrier gas. The purifed sample is charged in a vacuum vapour deposition apparatus (Balzers) and sublimed at a growth rate of 0.1 nm/s. Chamber pressure typically is $6\times10^{-6}$ Torr at the start and end of the deposition. The film thickness is measured by a quartz crystal monitor to give a total thickness of 50 nm.

B) Field-Effect Transistors

Bottom-gate thin-film transistor (TFT) structures with p-Si gate (10 Ω·cm) are used for all experiments. A high-quality thermal $SiO_2$ layer of 300 nm thickness serves as gate-insulator of $C_i$=11 $nF/cm^2$ capacitance per unit area. Source and drain electrodes are patterned by photolithography directly on the gate-oxide (bottom-contact configuration). Au source/drain electrodes defining channels of width W=2 mm and length L=50 µm are used. Prior to the deposition of the organic semiconductor, the $SiO_2$ surface is derivatized with hexamethyldisilazane (HMDS) by exposing it to saturated silane vapour at 160° C. for 2 hours.

Transistor Performance:

The thin-film transistors show clear p-type transistor behavior. From a linear fit to the square root of the saturated transfer characteristics, a high field-effect mobility is determined (IEEE Standard 1620). With a 300 nm gate-oxide of 11 $nF/cm^2$ capacitance per unit area the transistors show a threshold voltage of about −20 V.

The transistors show good on/off current ratios of $10^4$ to $10^5$.

EXAMPLE 5A

Thin-film Transistor by Vacuum Deposition of Product from Example 2

A highly doped Si-wafer with 300 nm thermally grown $SiO_2$ is cut and cleaned with hot acetone and hot isopropanol. The sample is immersed in piranha-solution (30% hydrogen peroxide in 70% sulfuric acid) for 10 minutes and thoroughly washed with ultra pure water (18.2 MΩcm). Subsequently, the $SiO_2$ surface is treated with octadecyltrichlorosilane (OTS) by a vapour prime process. For this process, the sample and ~0.3 ml of OTS are heated to 125° C. in a vacuum for three hours. The product from example 2 is evaporated on the sample through a shadow mask in a high vacuum (base pressure $2\times10^{-6}$ mbar). The substrate is kept at a temperature of 75° C. during the deposition. The deposition rate and the film thickness are measured with a water-cooled quartz crystal in the chamber. 50 nm of the product of example 2 is deposited at a rate of 0.5 Å/s. Gold contacts are vacuum-evaporated onto the formed thin-film in a separate chamber resulting in multiple thin-film transistor test structures on the sample with a channel length of 100 µm and a channel width of 500 µm.

Device characteristics are measured in a dry He atmosphere using a HP 4155A semiconductor parameter analyzer. For the transfer characteristic, the gate voltage $V_g$ is swept to −60 V and back in steps of 0.5 V, while keeping the drain voltage at $V_d$=−50 V. The transfer characteristics are analyzed in terms of non-contact corrected saturation field-effect mobility, onset voltage, threshold voltage, off-current and on-off ratio. Additionally, the output characteristics of the same device are measured.

The left part of FIG. 2 contains the transfer characteristics both on a linear scale and on a logarithmic scale. The mobility is µ=$1.7\times10^{-3}$ $cm^2/Vs$. The onset voltage of the device is small and negative ($V_{on}$=−1.3 V) and the threshold voltage is $V_t$=−2.5 V. The off-current $I_{off}$ is ~$1\times10^{-11}$ A and the on-off current ratio $I_{on}/I_{off}$ is $1\times10^4$. The right part of FIG. 2 presents the output characteristics and clearly shows the p-type operation of the device.

EXAMPLE 6

Influence of the Substrate Temperature on TFT

Thin-film transistors are made from the product of example 2 as described in example 5. The substrates are kept at various substrate temperatures during thin-film deposition. Approximately three devices are characterized on each sample according to the description in Example 5.

The table summarizes average transistor parameters for each sample and shows that the mobility is higher for samples kept at a lower temperature during the deposition process. Average field-effect mobilities of $1.3\times10^{-2}$ $cm^2/Vs$ are possible in thin-films of the product of example 2 deposited at T=0° C.

TABLE 1

Transistor parameters for films deposited at temperature T

| T [° C.] | µ [$cm^2/Vs$] | $V_{ON}$ [V] | $V_t$ [V] | $I_{off}$ [A] | $I_{on}/I_{off}$ |
|---|---|---|---|---|---|
| 0 | $8.5 \times 10^{-3}$ | −0.6 | −4.5 | $1 \times 10^{-11}$ | $5 \times 10^4$ |
| 30 | $8.7 \times 10^{-3}$ | +1.8 | −1.4 | $5 \times 10^{-10}$ | $5 \times 10^3$ |
| 45 | $6.4 \times 10^{-3}$ | +2.3 | −3.2 | $5 \times 10^{-11}$ | $1 \times 10^4$ |
| 75 | $2.2 \times 10^{-3}$ | −0.2 | −1.7 | $1 \times 10^{-11}$ | $1 \times 10^4$ |
| 90 | $9.5 \times 10^{-4}$ | +0.9 | −0.9 | $1 \times 10^{-11}$ | $5 \times 10^3$ |

EXAMPLE 7

Effect of the OTS Surface Treatment

Thin-film transistors from the product of example 2 are prepared as described in example 5 on a sample with OTS and on a reference sample. The reference sample is taken from the same wafer and is cleaned with the normal sample. After the cleaning, the reference sample is not subjected to the surface treatment with OTS. The reference sample is installed close to the sample with OTS in the deposition chamber and the product of example 2 is evaporated on both samples at a fixed substrate temperature of T=0° C. in the same deposition run.

FIG. 3 shows transfer characteristic from the sample with OTS and from the reference sample (without OTS). The surface treatment leads to a large gain in device quality. The table contains transistor parameters from both devices. The mobility with OTS is $1.0\times10^{-2}$ $cm^2/Vs$ and the mobility from the reference sample is $2.0\times10^{-5}$ $cm^2/Vs$ (see Table 2), i.e. lower by a factor of 500.

TABLE 2

Transistor parameters with and without substrate surface treatment

| Sample | µ [$cm^2/Vs$] | $V_{ON}$ [V] | $V_t$ [V] | $I_{off}$ [A] | $I_{on}/I_{off}$ |
|---|---|---|---|---|---|
| with OTS | $1.0 \times 10^{-2}$ | −0.5 | −4 | $<5 \times 10^{-12}$ | $1 \times 10^5$ |
| without OTS (reference sample) | $2.0 \times 10^{-5}$ | −12.6 | ~−12 | $1 \times 10^{-12}$ | $5 \times 10^2$ |

EXAMPLE 8

Stability of Devices Made from the Product of Example 2 in Comparison to Pentacene Transistors Pentacene thin-film transistors are made in an identical fashion by depositing pentacene on a sample held at 80° C., due to the fact that, in the case of pentacene on OTS, elevated substrate temperatures lead to higher field-effect mobilities (K. P. Pernstich et al., J. Appl. Phys. 96, 6431 (2004)). FIG. 4 compares a pentacene device with the transistor from example 5 (prepared using the semiconducting product of example 2). Both devices are measured in a dry He atmosphere. The transistor made from the material of example 2 shows a current hysteresis smaller compared to the one of the pentacene transistor. For the pentacene device, the current at 5 V above the onset voltage (i.e. at $V_g=-14$ V) is $I_d=-5.4\times 10^{-9}$ A. The device is influenced by the subsequent steps of the measurement and in the reverse sweep a current of the same magnitude is obtained at $V_g=-17.3$ V. The shift is $\Delta V_g=-3.3$ V. In the case of the transistor made from the product of example 2, the current at 5 V above onset (at $V_g=-5.5$ V) is $I_d=-1.5\times 10^{-9}$ A. The corresponding shift from the reverse sweep is $\Delta V_g=-1.1$ V, i.e. it is lower by a factor of 3 and more in conformance with the desired reversability.

EXAMPLE 9

3,10-Dimethoxy-7,14-bis-(4-methoxy-phenyl)-chromeno[2,3-b]xanthene

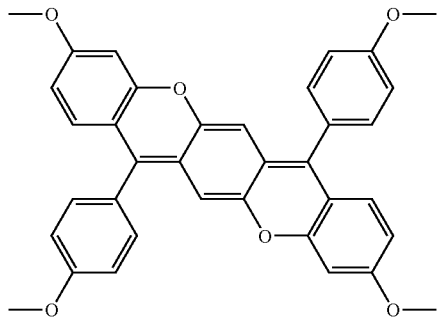

a) Synthesis of the precursor 2,5-Bis-[methoxy-bis-(4-methoxy-phenyl)-methyl]-benzene-1,4-diol:

A 250 ml Schlenk flask is charged with 1,4-bis-(1-ethoxy-ethoxy)-benzene (10.16 g, 40 mmol) and flushed with nitrogen. Then diethyl ether (50 ml), n-BuLi (29.6 ml of a 2.7 N solution in heptane, 80 mmol) and N,N,N',N'-tetramethyl ethylenediamine (9.3 g, 80 mmol). are added. The temperature increases to 35° C., and the mixture becomes cloudy. After stirring over night the mixture turns into a thick slurry. To this is added dropwise a solution of bis-(4-methoxy-phenyl)-methanone (19.4 g, 80 mmol) in hot THF (150 ml). After the addition of the ketone is complete, the mixture is heated at reflux for one hour. The solvent is then removed, and to the residue is added methanol (ca. 150 ml) and evaporated. This is repeated again, and then the residue is slurried up in methanol (ca. 150 ml). Hydrochloric acid is added (14 ml of 32% acid), and the formed suspension is stirred at ambient temperature for 45 minutes. The solvent is evaporated, and the residue is slurried up again in methanol. Another portion of hydrochloric acid (2 ml of 32% acid) is added, and the mixture kept stirred for two hours at ambient temperature, and then filtered. The solid is washed with methanol for three times (ca. 30 ml each), and dried to give 19.9 g of pink crystals.

b) A flask is charged with 2,5-Bis-[methoxy-bis-(4-methoxy-phenyl)-methyl]-benzene-1,4-diol (18.06 g, 29 mmol) and nitrobenzene (35 ml) and heated at 195° C. (bath temperature) for two hours. The dark violet coloured mixture is then allowed to cool to ambient temperature and stirred for three hours. The product is then filtered off, and washed for three times with toluene (ca. 10 ml each portion) and finally dried in vacuum to give the product as deep violet crystals, 5.45 g (32%). The DSC of this material shows a transition at 255° C. and a melting point of 338° C. The structure is confirmed by X-ray crystallography, space group P-1, a=9.424(4); b=11.815(5); c=12.571(5); cell angles: α=110.315(16); β=97.897(19); γ=93.76(2).

EXAMPLE 10

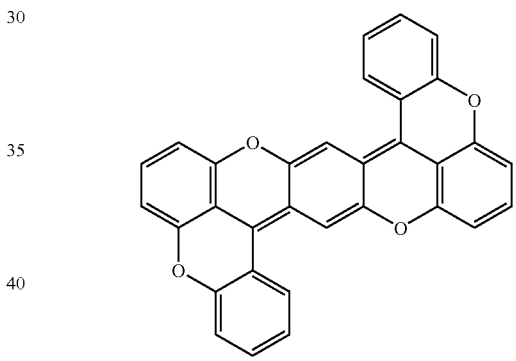

A 500 ml Schlenk flask is charged with 1,4-bis-(1-ethoxy-ethoxy)-benzene (10.16 g, 40 mmol) and flushed with nitrogen. Then diethyl ether (50 ml), n-BuLi (55 ml of a 1.6 N solution in hexanes, 88 mmol) and N,N,N',N'-tetramethyl ethylenediamine (9.3 g, 80 mmol) are added. A slight temperature increase is observed, and the mixture becomes cloudy. After stirring over night, the mixture has become a thick slurry to which a solution of xanthone (15.3 g, 80 mmol) in warm THF (ca. 150 ml) is added dropwise within 10 minutes. In a slightly exothermic reaction, temporarily a brown solution is formed, from which a colourless solid precipitates. This suspension is stirred for another hour, and then the solvent is removed on the rotavapor. The residue is re-dissolved in methanol (ca. 500 ml) and ca. 20 ml of 32% HCl is added to the mixture. After stirring for ca. one hour, the colorless precipitate is filtered off and dried (12.4 g). This material is used directly for the following reaction.

A 100 ml flask is charged with 12.0 g of the product obtained as described above and nitrobenzene (70 ml). This mixture is heated initially at 180° C., where the colourless material dissolves and forms a deeply blue coloured solution. Heating at 180° C. is maintained for ca. one hour and then the mixture is refluxed for another hour to form a suspension of a solid. The mixture is allowed to cool over night to ambient temperature and then filtered. The solid (deeply violet-blue crystals with a green luster) is washed free from nitrobenzene with copious amounts of ethanol and dried to give 5.89 g of product, mp.=436.8° C. (DSC), ms (M/z, relative abundance in %), peaks >5%:466 (7.18), 465 (34.5), 464 (100), 435 (5.9), 232 (25.4), 203 (5.3), 55 (5.9).

EXAMPLE 11

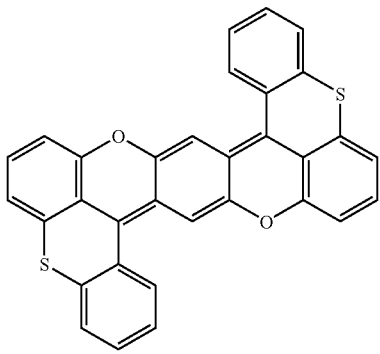 [SMILES: c1cc2oc3ccccc3c3c4cc5oc6cccc7oc8ccccc8c(c5cc4oc(c1)c2-3)-c76]

A 500 ml Schlenk flask is charged with 1,4-bis-(1-ethoxy-ethoxy)-benzene (10.16 g, 40 mmol) and flushed with nitrogen. Then diethyl ether (50 ml), n-BuLi (55 ml of a 1.6 N solution in hexanes, 88 mmol) and N,N,N',N'-tetramethyl ethylenediamine (9.3 g, 80 mmol) are added. After stirring over night the mixture becomes a thick slurry to which a solution of thioxanthone (17.38 g, 80 mmol) in warm THF (ca. 200 ml) is added dropwise within 10 minutes. In a slightly exothermic reaction, a brown solution is formed. This suspension is refluxed for half an hour, and then the solvent is removed on the rotavapor. The residue is re-dissolved in methanol (ca. 500 ml) and ca. 20 ml of 32% HCl is added to the mixture. A pink solid precipitates and is filtered off and dried (17.4 g). This material is used directly for the next reaction.

A 100 ml flask is charged with 17.4 g of the product obtained as described above and nitrobenzene (70 ml). After heating the mixture to 180° C., a deeply blue coloured solution is obtained. Heating at 180° C. is maintained for ca. one hour and then the mixture is refluxed for another hour to give a thick suspension of a bluish black solid in a blue solution. The mixture is allowed to cool over night to ambient temperature and then filtered. The solid (violet blue crystals with a green luster) is washed free from nitrobenzene with copious amounts of ethanol and dried (8.9 g). This material is extracted over ca. 60 hours in a Soxleth extractor with toluene. The material remaining in the extraction thimble is rinsed out with ethanol and collected on a filter to give, after drying, a deeply violet coloured solid (translucent green under the microscope), mp.=437.3° C. (DSC), ms (M/z, relative abundance in %), peaks >5%: 499 (7.62), 498 (24.7), 497 (43.2), 496 (100), 464 (10.70), 432 (9.1), 248 (23.5), 232 (8.4), 216 (8.9).

EXAMPLE 12

3,10-Diethoxy-7,14-bis-(4-ethoxy-phenyl)-chromeno [2,3-b]xanthene

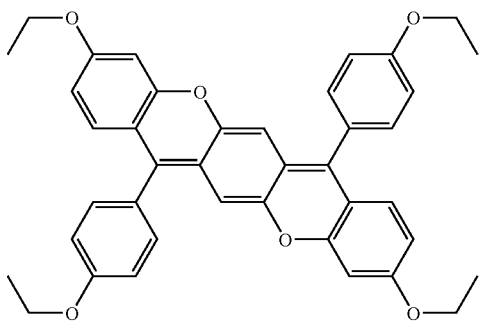 [SMILES: CCOc1ccc(C2=c3cc4c(cc3Oc3cc(OCC)ccc32)=C(c2ccc(OCC)cc2)c2ccc(OCC)cc2O4)cc1]

a) Synthesis of the precursor 2,5-Bis-[bis-(4-ethoxy-phenyl)-methoxy-methyl]-benzene-1,4-diol: This compound is prepared in an analogous manner as described in example 9. From 10.16 g of 1,4-bis-(1-ethoxy-ethoxy)-benzene (40 mmol) and bis-(4-ethoxy-phenyl)-methanone (21.6 g, 80 mmol) 17.95 g (66%) of the product is obtained.

b) A flask is charged with 2,5-Bis-[bis-(4-ethoxy-phenyl)-methoxy-methyl]-benzene-1,4-diol (16.97 g, 25 mmol) and nitrobenzene (30 ml) and heated at 195° C. (bath temperature) for two hours. The dark violet coloured mixture is then allowed to cool to ambient temperature. The product is then filtered off, and washed for three times with nitrobenzene (ca. 7 ml each time) and three times with toluene (ca. 8 ml each time) and finally dried in vacuum to give the product as deep violet crystals, 6.03 g (39%). The DSC of this material shows a mp. of 302° C. The structure of the material was confirmed by X-ray crystallography; space group: P-1; a=7.483(6); b=8.710(7); c=12.618(7); α=91.22(5) β=92.43(5) γ=110.35 (5).

EXAMPLE 13

7,14-Diphenyl-5,12-dithia-pentacene

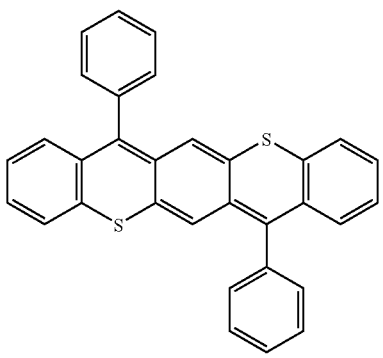 [SMILES: c1ccc(C2=c3cc4c(cc3Sc3ccccc32)=C(c2ccccc2)c2ccccc2S4)cc1]

The synthesis of the precursor 7,14-Diphenyl-7,14-dihydro-5,12-dithia-pentacene is performed in analogy to Freund, T. et al., *Angew. Chem.* 1994, 106, 2547 (see scheme below).

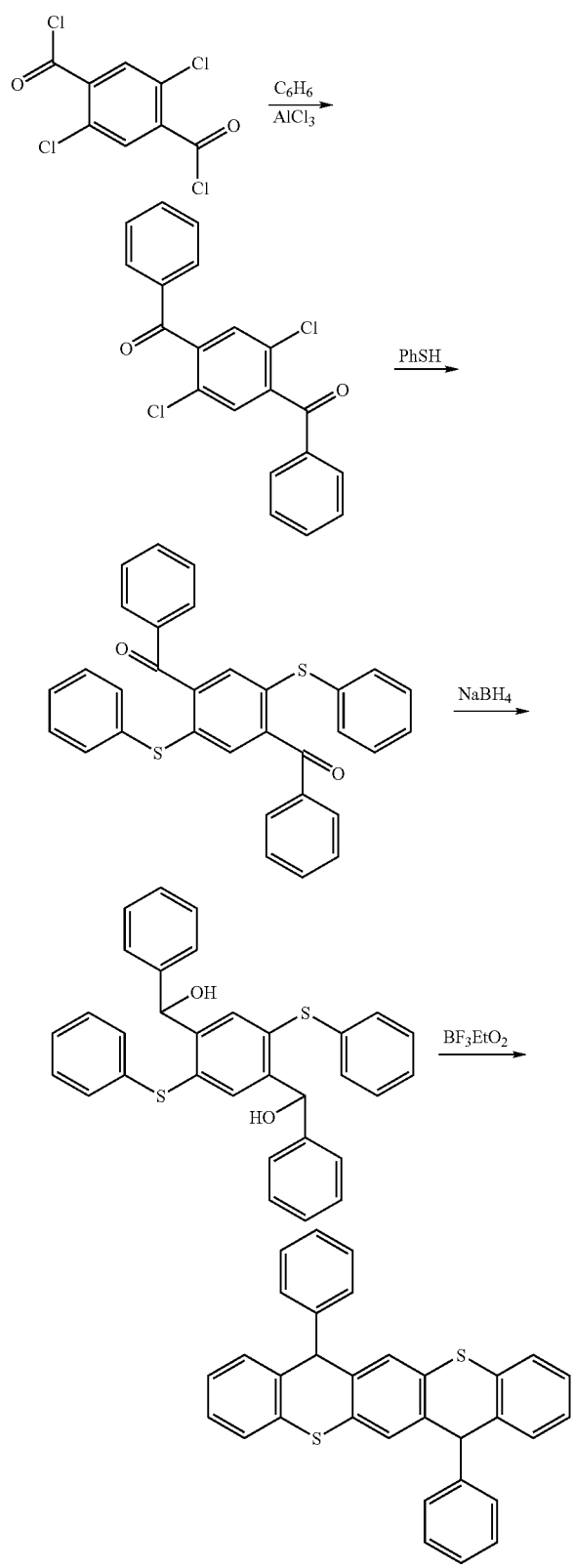

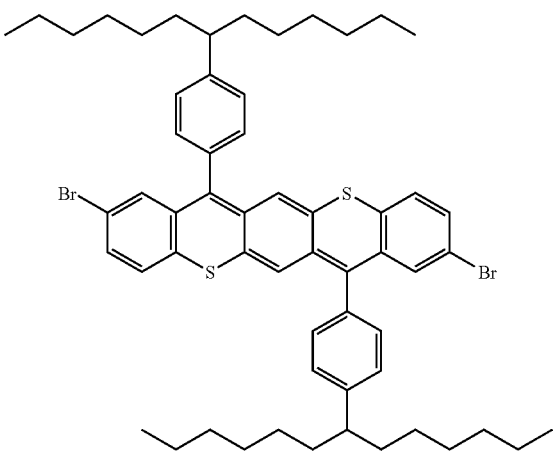 [SMILES: CCCCCCC(CCCCCC)c1ccc(C2=c3cc4c(cc3Sc3ccc(Br)cc32)=C(c2ccc(C(CCCCCC)CCCCCC)cc2)c2cc(Br)ccc2S4)cc1]

ortho-dichlorobenzene, twice with 15 ml toluene and finally with 30 ml of ethanol. After drying 5.9 g of 7,14-Diphenyl-5,12-dithia-pentacene is obtained as dark violet crystals, mp=320° C. EI-MS: 468 (100%), 436 (7%), 391 (7%), 358 (8%), 234 (11%). The structure is confirmed by single crystal X-ray diffraction analysis: (space group: P-1; cell length: a 5.746(2); b 10.337(2); c 10.623(2); cell angles: α 116.620(11) β 104.914(13) γ 92.354(14)). FIG. 5 shows representations of the product calculated according to the above x-ray data (views other than along crystallographic axes).

EXAMPLE 14

Field-Effect Transistors from 7,14-Diphenyl-5,12-dithia-pentacene

Bottom-gate thin-film transistor (TFT) structures with p-Si gate (10 Ωcm) are used for all experiments. A high-quality thermal $SiO_2$ layer of 300 nm thickness serves as gate-insulator of $C_i$=11 $nF/cm^2$ capacitance per unit area. Source and drain electrodes are patterned by photolithography directly on the gate-oxide (bottom-contact configuration). Au source/drain electrodes defining channels of width W=2 mm and length L=4-30 μm are used. Prior to the deposition of the organic semiconductor, the $SiO_2$ surface is derivatized with hexamethyldisilazane (HMDS) by exposing it to saturated silane vapour at 160° C. for 2 hours.

Transistor Performance:

The thin-film transistors show clear p-type transistor behavior (see FIG. 6). From a linear fit to the square root of the saturated transfer characteristics, a field-effect mobility between 0.5-1.9 $10^{-3}$ $cm^2/Vs$ is determined (IEEE Standard 1620). With a 300 nm gate-oxide of 11 $nF/cm^2$ capacitance per unit area the transistors show a threshold voltage of about −20 V. The transistors show good on/off current ratios of 0.1-5 $10^6$.

EXAMPLE 15

2,9-Dibromo-7,14-bis-[4-(1-hexyl-heptyl)-phenyl]-5,12-dithia-pentacene

A mixture of 8.0 g of 7,14-diphenyl-7,14-dihydro-5,12-dithia-pentacene and 3.1 grams of chloranil is heated in 70 ml ortho-dichlorobenzene to 150° C. for one hour. After cooling to 22° C., the product is filtered off and washed with 30 ml of The synthesis of the precursor 2,9-Dibromo-7,14-bis-[4-(1-hexyl-heptyl)-phenyl]-7,14-dihydro-5,12-dithia-pentacene is performed in analogy to Freund, T. et al. *Angew. Chem.* 1994, 106, 2547 with 1-hexyl-heptyl-benzene and p-bromo-thiophenol as corresponding starting materials.

A mixture of 7.1 grams of 2,9-Dibromo-7,14-bis-[4-(1-hexyl-heptyl)-phenyl]-7,14-dihydro-5,12-dithia-pentacene and 2.6 grams of chloranil is heated in 100 ml ortho-dichloronezene at 150° C. for 4 hours. After cooling to 22° C., the reaction mixture is poured into 600 ml methanol, filtered off and washed three times with 50 ml methanol. The crude product is suspended in 80 ml acetone, stirred for one hour and filtered off. After drying in vacuum 3.0 grams 2,9-dibromo-7,14-bis-[4-(1-hexyl-heptyl)-phenyl]-5,12-dithia-pentacene are obtained as violet crystals. $^1$H-NMR(CHCl$_3$): 7.26 (d, 4H, J=8 Hz); 7.04 (d, 4H, J=8 Hz); 6.98 (dd, 2H, J=8.5/2 Hz); 6.71 (d, 2H, J=8.5 Hz); 6.58 (d, 2H, J=2 Hz); 5.86 (s, 2H); 2.57 (m, 2H); 1.8-1.1 (m, 40H); 0.88 (t, 12H).

EXAMPLE 16

2,5-Bis-phenylsulfanyl-benzene-1,4-dicarbaldehyde

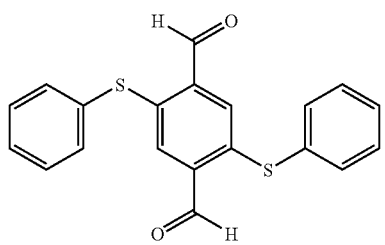 [SMILES: O=Cc1cc(Sc2ccccc2)c(C=O)cc1Sc1ccccc1]

A 500 ml Schlenk flask is charged under an inert atmosphere with 2,5-Dichloro-benzene-1,4-dicarbaldehyde (30.45 g, 0.15 mol), potassium carbonate (62.1 g, 0.45 mol) and dry DMF (200 ml). The flask is immersed in an oil bath of 80° C., and then without delay thiophenol (33.0 g, 0.3 mol) is added via a dropping funnel within 15 minutes. To the formed brown suspension is added water (ca. 100 ml) and the mixture is stirred for another 5 minutes. Then the contents of the flask are poured as a thin stream into a beaker which contain 2 L of vigorously stirred water. A yellow solid precipitates, and the mixture is stirred for another hour. The solid is then filtered off, washed with water (twice 250 ml), and recrystallised without further drying from THF (ca. 200 ml). The crystals of the product are filtered off, washed with little iso-propanol (ca. 50 ml) and dried to give the product (36.75 g). From the mother liquors most of the THF is removed on the rotavapor which leads to the crystallisation of another crop. This material is also filtered off and washed with little iso-propanol to give another 4.72 g of product. Bright yellow crystals, mp. 163° C. $^1$H-NMR (CDCl$_3$, 300 MHz) δ 7.39 (phenyl para H); 7.40 (phenyl ortho H)); 7.41 (phenyl meta H); 7.58 (s, aryl CH); 10.27 (s, 1H, CHO). $^{13}$C-NMR (CDCl$_3$, 75 MHz) δ 129.18 (phenyl para CH); 130.19 (phenyl ortho CH); 132.47 (phenyl ipso C); 133.20 (phenyl meta CH); 133.75 (aryl CH); 136.79 (CCHO); 139.54 (CS); 190.45 (CHO).

EXAMPLE 17

5,12-Dithia-pentacene D

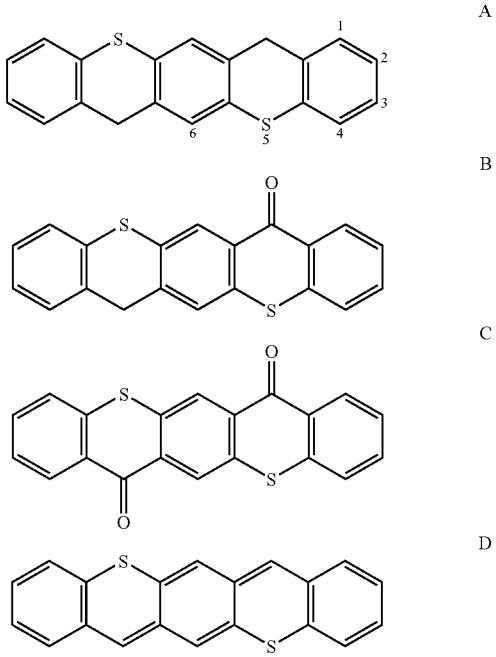

a) Synthesis of the mixture of precursors A, B, and C: A 500 ml round bottom flask is charged with sulphuric acid (ca. 200 ml 96% acid). To the vigorously stirred acid is added slowly via spatula 10.0 g (28.57 mol) of 2,5-Bis-phenylsulfanyl-benzene-1,4-dicarbaldehyde. The colour turns instantly into dark olive green, and the temperature of the mixture rises to ca. 30° C. The mixture is stirred for another 10 minutes and then poured as a thin stream into a beaker with 800 ml of vigorously stirred water. A yellow brown solid precipitates, which is filtered off, and washed thoroughly with water (ca. 300 ml). The solid is then slurried in hot ethanol (ca. 150 ml) and filtered off again. The moist filter cake is slurried again with refluxing THF (ca. 100 ml) and then filtered off to give after drying 5.86 g of product. Another crop of 3.20 g is obtained from the concentrated ethanol- and THF-filtrates. The obtained material is a mixture of A, B, and C as determined by mass spectroscopy, yield 9.06 g (95%).

b) Synthesis of 7,14-Dihydro-5,12-dithia-pentacene A (alternative): A 500 ml flask is charged with the above mixture and THF (ca. 200 ml) and flushed with nitrogen. After heating the solvent to 60° C., borane dimethyl sulfide adduct (4 ml 96%, ca. 40 mmol) is added, and the mixture stirred for three hours. Then another portion of borane dimethyl sulfide adduct (2 ml 96%, ca. 20 mmol) is added, and the mixture stirred for another three hours at 60° C. During this time the colour of the reaction mixture turns from yellow to almost colourless. After cooling over night the formed solid is filtered off, and dried to give 8.03 g (92.8%) of colourless crystals, mp.=271° C. (DSC). $^1$H-NMR (DMSO-D6, 120° C., 300 MHz) δ 3.86 (s, 2H, CH$_2$); 7.21, 7.23 (2 "tr", 1 each, H-3, H4); 7.37, 7.43 (2 d, 1 each, H-2, H-4); 7.49 (s, 1H, H-7).

c) Synthesis of 5,12-Dithia-pentacene D: A 40 ml autoclave is charged with A (0.718 g), sulfur (0.217 g), pyridine (10 ml) and a magnetic stirrer bar. After sealing, the autoclave is heated to 240° C. over night (52 bar) and then allowed to cool to ambient temperature. The reaction product is then filtered off and dried to give 0.66 g of the deep reddish black product (mp 276-280° C. (DSC); yield 92%).

The invention claimed is:
1. A semiconductor device selected from the group consisting of a diode, an organic field effect transistor, a solar cell, or a device containing a diode, and/or organic field effect transistor and/or solar cell comprising a non-polymeric compound as an organic semiconductor, wherein said compound is a quinoid diheteroacene of the formula I

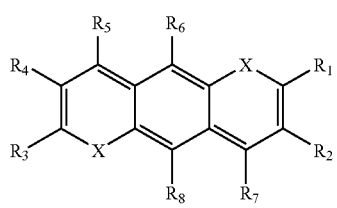

wherein X is O, S or NR,
each of R, $R_1$, $R_2$, $R_3$, $R_4$, $R_5$, $R_6$, $R_7$, $R_8$ independently are an organic residue, or 2 or more thereof together form one or more annealed rings which may be substituted or unsubstituted, carbocyclic or heterocyclic, aromatic, quinoid or aliphatic;
and $R_1$, $R_2$, $R_3$, $R_4$, $R_5$, $R_6$, $R_7$, $R_8$ further may be hydrogen with proviso that formula (1) excludes a boron complex.

2. Semiconductor device of claim 1, wherein the compound of the formula I is of a molecular weight of less than 1200 g/mol and belongs to the symmetry group $C_s$.

3. Semiconductor device of claim 1, where in the compound of the formula I R is selected from the group consisting of unsubstituted or substituted alkyl, unsubstituted or substituted alkenyl, unsubstituted or substituted alkynyl, and unsubstituted or substituted aryl; each of $R_1$, $R_2$, $R_3$, $R_4$, $R_5$, $R_6$, $R_7$, $R_8$ independently is selected from the group consisting of H, unsubstituted or substituted alkyl, unsubstituted or substituted alkenyl, unsubstituted or substituted alkynyl, unsubstituted or substituted aryl, halogen, substituted silyl, and $XR_{12}$; or one or more of R, $R_1$, $R_2$, $R_3$, $R_4$, $R_5$, $R_6$, $R_7$, $R_8$, together with the carbon or nitrogen atoms they are bonding to, form a saturated or unsaturated, unsubstituted or substituted carbocyclic or heterocyclic annealed ring;
$R_{12}$ is unsubstituted or substituted alkyl, unsubstituted or substituted alkenyl, unsubstituted or substituted alkynyl, substituted silyl, or unsubstituted or substituted aryl.

4. Semiconductor device of claim 1, wherein in formula I each alkyl is $C_1$-$C_{22}$alkyl, which may be interrupted by O, S, COO, OCNR10, OC(O)O, OC(O)NR10, NR10CNR10, or NR10, where —$R^{10}$ is H, $C_1$-$C_{12}$alkyl, or $C_3$-$C_{12}$cycloalkyl;
each aryl is $C_4$-$C_{18}$aromatic moieties, which may contain, as part of the ring structure, one or 2 heteroatoms selected from O, N and S;
annealed rings, where present, are formed by 2 or more of the residues $R_1$, $R_2$, $R_3$, $R_4$, $R_5$, $R_7$, $R_8$, and are aromatic carbocyclic or N-heterocyclic, substituted or unsubstituted 6-membered rings;
substituents, where present, bond to a carbon atom and are selected from the group consisting of $C_1$-$C_{22}$alkoxy, $C_1$-$C_{22}$alkyl, $C_4$-$C_{12}$cycloalkoxy, $C_3$-$C_{12}$cycloalkyl, OH, halogen, $Si(R11)_3$, phenyl, and naphthyl; while saturated carbons also may be substituted by oxo (=O); 2 adjacent substituents may be linked together to form a lactone, anhydride, imide or carbocyclic ring.

5. Semiconductor device according to claim 1, where the compound of the formula I is of formula II

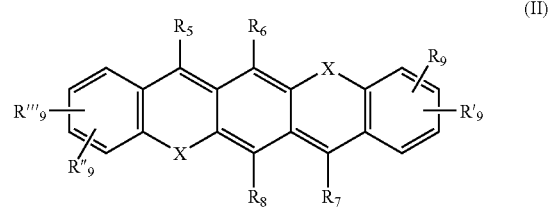

wherein
X is O, S or NR,
R is selected from the group consisting of unsubstituted or substituted $C_1$-$C_{18}$alkyl, unsubstituted or substituted $C_2$-$C_{18}$alkenyl, unsubstituted or substituted $C_2$-$C_{18}$alkynyl, and unsubstituted or substituted $C_4$-$C_{18}$aryl;
each of $R_5$, $R_6$, $R_7$, $R_8$ independently is selected from the group consisting of H; unsubstituted or substituted $C_1$-$C_{22}$alkyl or $C_2$-$C_{22}$alkenyl, each of which may be interrupted by O, S, COO, OCNR10, OCOO, OCONR10, NR10CNR10, or NR10; substituted $C_2$-$C_{18}$alkynyl; unsubstituted or substituted $C_4$-$C_{18}$aryl; halogen; silyl; and $XR_{12}$;
$R_9$, $R'_9$, $R''_9$, $R'''_9$ independently are as defined for $R_5$,
or adjacent $R_9$ and $R'_9$ and/or adjacent $R''_9$ and $R'''_9$, or $R_5$ and $R'''_9$, and/or $R_7$ and $R'_9$, together form an annealed ring;
—$R^{10}$ is H, $C_1$-$C_{12}$alkyl, or $C_4$-$C_{12}$cycloalkyl;
each silyl is $SiH(R11)_2$ or $Si(R11)_3$ with —$R^{11}$ being $C_1$-$C_{20}$-alkyl or -alkoxy;
$R_{12}$ is silyl, acyl, unsubstituted or substituted $C_1$-$C_{22}$alkyl, or unsubstituted or substituted $C_4$-$C_{18}$aryl;
each aryl is $C_4$-$C_{18}$aromatic moieties, which may contain, as part of the ring structure, one or 2 heteroatoms selected from O, N and S;
annealed rings, where present, are aromatic carbocyclic or N-heterocyclic, substituted or unsubstituted 6-membered rings; and
substituents, where present, bond to a carbon atom and are selected from the group consisting of $C_1$-$C_{22}$alkoxy, $C_1$-$C_{22}$alkyl, $C_4$-$C_{12}$cycloalkoxy, $C_4$-$C_{12}$cycloalkyl, OH, halogen, phenyl, and naphthyl; while saturated carbons also may be substituted by oxo (=O); 2 adjacent substituents may be linked together to form a lactone, anhydride, imide or carbocyclic ring.

6. Semiconductor device of claim 5, where in the compound of the formula II X is O, S or NR,
R is selected from the group consisting of $C_1$-$C_{18}$alkyl, unsubstituted or substituted phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, and benzothienyl;

each of $R_5$, $R_6$, $R_7$, $R_8$ independently is selected from the group consisting of H; unsubstituted or substituted $C_1$-$C_{18}$alkyl, $C_2$-$C_{18}$alkenyl or $C_1$-$C_{18}$alkoxy, each of which may be interrupted by O, S, or NR10; substituted ethynyl; unsubstituted or substituted phenyl, naphthyl, pyridyl, tetrahydronaphthyl, furyl, thienyl, pyrryl, chinolyl, isochinolyl, anthrachinyl, anthracenyl, phenanthryl, pyrenyl, benzothiazolyl, benzoisothiazolyl, benzothienyl; halogen; and Si(R11)$_3$;

$R_9$, R'$_9$, R''$_9$, R'''$_9$ independently are as defined for $R_5$, or adjacent $R_9$ and R'$_9$ and/or adjacent R''$_9$ and R'''$_9$ together form an annealed ring; or $R_5$ as unsubstituted or substituted phenyl is linked to R'''$_9$, and/or $R_7$ as unsubstituted or substituted phenyl is linked to R'$_9$, forming a 6-membered ring structure with R'''$_9$ and/or R'$_9$ being X or CH$_2$;

—$R^{10}$ is H, $C_1$-$C_{12}$alkyl, or $C_4$-$C_{12}$cycloalkyl;

—$R^{11}$ is methyl, ethyl, propyl, methoxy, ethoxy, or propoxy;

annealed rings, where present, are aromatic carbocyclic or N-heterocyclic, substituted or unsubstituted 5- or 6-membered rings; and substituents, where present, bond to a carbon atom and are selected from the group consisting of $C_1$-$C_{18}$alkoxy, $C_1$-$C_{18}$alkyl, $C_4$-$C_{12}$cycloalkoxy, $C_4$-$C_{12}$cycloalkyl, OH, halogen, phenyl, and naphthyl; while saturated carbons also may be substituted by oxo (=O); 2 adjacent substituents may be linked together to form a lactone, anhydride, imide or carbocyclic ring.

7. Semiconductor device of claim 6, where in the compound of the formula II X is O or S;

each of $R_5$, $R_6$, $R_7$, $R_8$ independently is selected from the group consisting of H; unsubstituted or substituted $C_1$-$C_{18}$alkyl or $C_1$-$C_{18}$alkoxy; substituted ethynyl; unsubstituted or substituted phenyl, naphthyl, pyridyl, chinolyl; halogen; and Si(R11)$_3$;

$R_9$, R'$_9$, R''$_9$, R'''$_9$ independently are as defined for $R_5$, or adjacent $R_9$ and R'$_9$ and/or adjacent R''$_9$ and R'''$_9$, together with the connecting carbon atoms, form an annealed phenyl, naphthyl or pyridyl ring; or $R_5$ as unsubstituted or substituted phenyl is linked to R'''$_9$, and/or $R_7$ as unsubstituted or substituted phenyl is linked to R'$_9$, forming a 6-membered ring structure with R'''$_9$ and/or R'$_9$ being X;

—$R^{11}$ is methyl, ethyl, propyl, methoxy, ethoxy, or propoxy; and substituents, where present, bond to a carbon atom and are selected from the group consisting of $C_1$-$C_{18}$alkoxy, $C_1$-$C_{18}$alkyl, cyclohexyloxy, cyclopentyloxy, cyclohexyl, cyclopentyl, halogen, phenyl, and naphthyl; while saturated carbons also may be substituted by oxo (=O).

8. Process for the preparation of an organic semiconductor device, which process comprises applying a compound of the formula I of claim 1;

to a suitable substrate, wherein the deposition of the compound is effected by vapour deposition.

9. Process for the preparation of an organic semiconductor device, which process comprises the heating of a layer of a precursor compound of the formula III

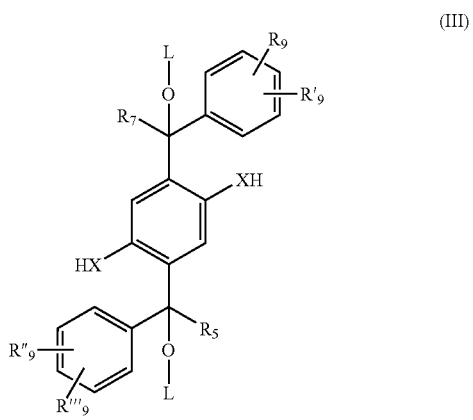

(III)

wherein $R_5$, $R_7$, $R_9$, R'$_9$, R''$_9$, R'''$_9$ and X are as defined for formula II in claim 5; and L is $C_1$-$C_8$alkyl, to a temperature in the range 60-500° C.

10. The process according to claim 8, wherein the semiconductor is an organic thin film transistor, wherein the film comprises the compound of formula I and is formed having a thickness in the range of from 5 to 200 nm.

11. Compound of the formula II or IV

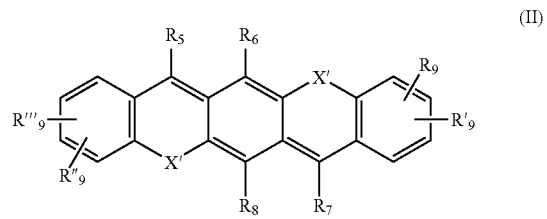

(II)

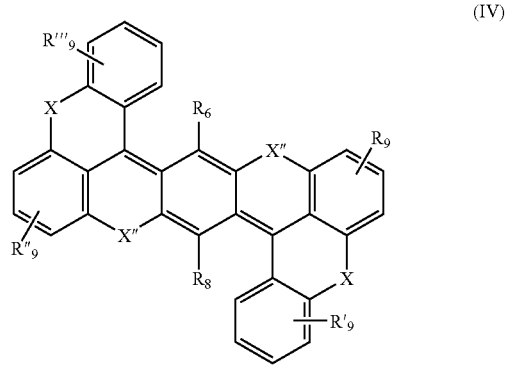

(IV)

wherein

X' is S or NR,

X and X'' independently are O, S or NR,

R is selected from the group consisting of unsubstituted or substituted $C_1$-$C_{18}$alkyl, unsubstituted or substituted $C_2$-$C_{18}$alkenyl, unsubstituted or substituted $C_2$-$C_{18}$alkynyl, and unsubstituted or substituted $C_4$-$C_{18}$aryl;

each of $R_5$, $R_6$, $R_7$, $R_8$ independently is selected from the group consisting of H; unsubstituted or substituted $C_1$-$C_{22}$alkyl or $C_2$-$C_{22}$alkenyl, each of which may be interrupted by O, S, COO, OCNR10, OCOO, OCONR10, NR10CNR10, or NR10; substituted $C_2$-$C_{18}$alkynyl; unsubstituted or substituted $C_4$-$C_{18}$aryl; halogen; Si(R11)$_3$; and XR$_{12}$;

$R_9$, $R'_9$, $R''_9$, $R'''_9$ independently are as defined for $R_5$, or, in formula II, adjacent $R_9$ and $R'_9$ and/or adjacent $R''_9$ and $R'''_9$ together form an annealed ring;

—$R^{10}$ is H, $C_1$-$C_{12}$alkyl, or $C_4$-$C_{12}$cycloalkyl;

—$R^{11}$ is $C_1$-$C_{20}$-alkyl or -alkoxy;

$R_{12}$ is Si($R^{11}$)$_3$, unsubstituted or substituted $C_1$-$C_{22}$alkyl, unsubstituted or substituted $C_4$-$C_{18}$aryl;

each aryl is selected from $C_4$-$C_{18}$aromatic moieties, which may contain, as part of the ring structure, one or 2 heteroatoms selected from O, N and S;

annealed rings, where present, are aromatic carbocyclic or N-heterocyclic, substituted or unsubstituted 6-membered rings; and substituents, where present, bond to a carbon atom and are selected from the group consisting of $C_1$-$C_{22}$alkoxy, $C_1$-$C_{22}$alkyl, $C_4$-$C_{12}$cycloalkoxy, $C_4$-$C_{12}$cycloalkyl, OH, halogen, phenyl, and naphthyl; while saturated carbons also may be substituted by oxo (=O); 2 adjacent substituents may be linked together to form a lactone, anhydride, imide or carbocyclic ring.

12. Compound of claim 11, wherein

R is selected from the group consisting of $C_1$-$C_{18}$alkyl, unsubstituted or substituted phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, and benzothienyl;

each of $R_5$, $R_6$, $R_7$, $R_8$ independently is selected from the group consisting of H; unsubstituted or substituted $C_1$-$C_{18}$alkyl or $C_1$-$C_{18}$alkoxy, each of which may be interrupted by O, S, or NR10;

substituted ethynyl; unsubstituted or substituted phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, benzothienyl; halogen; and Si(R11)$_3$;

$R_9$, $R'_9$, $R''_9$, $R'''_9$ independently are as defined for $R_5$, or adjacent $R_9$ and $R'_9$ and/or adjacent $R''_9$ and $R'''_9$ together form an annealed ring;

—$R^{10}$ is H, $C_1$-$C_{12}$alkyl, or $C_4$-$C_{12}$cycloalkyl;

—$R^{11}$ is methyl, ethyl, propyl, methoxy, ethoxy, or propoxy;

annealed rings, where present, are aromatic carbocyclic or N-heterocyclic, substituted or unsubstituted 5- or 6-membered rings; and substituents, where present, bond to a carbon atom and are selected from the group consisting of $C_1$-$C_{18}$alkoxy, $C_1$-$C_{18}$alkyl, $C_4$-$C_{12}$cycloalkoxy, $C_4$-$C_{12}$cycloalkyl, OH, halogen, phenyl, and naphthyl; 2 adjacent substituents may be linked together to form a lactone, anhydride, imide or carbocyclic ring.

13. A method for the manufacture of an electronic device comprising an organic semiconductor wherein said method comprises incorporating into said electronic device an effective amount of a compound of the formula I according to claim 1.

14. Semiconductor device comprising a polymeric compound as an organic semiconductor, wherein said compound contains a quinoid diheteroacene of the formula I of claim 1.

15. Semiconductor device according to claim 5, wherein aryl is selected from the group consisting of phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl and benzothienyl.

16. Process for the preparation of an organic semiconductor device according to claim 8, wherein 1 or 2 of R1-R8 contain a residue selected from $C_4$-$C_{22}$alkyl, $C_{10}$-$C_{22}$-phenylalkyl, or said residues interrupted in the aliphatic part by O, S, NR10, COO, OCNR10, OCOO, OCONR10, NR10CNR10—$R^{10}$ is H, $C_1$-$C_{12}$cycloalkyl, OH, halogen, Si(R11)$_3$, phenyl and naphthyl.

17. Process for the preparation of an organic semiconductor device according to claim 8, wherein the deposition of the compound is effected by application of a solution in an organic solvent, followed by removal of the solvent.

18. A compound according to claim 11 wherein aryl is selected from the group consisting of phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl and benzothienyl.

19. A method according to claim 13 wherein said electronic device is selected from the group consisting of organic field effect transistor, thin film transistor, electronic device containing an organic field effect transistor and electronic device containing a thin film transistor.

20. Semiconductor device according to claim 14 comprising a polymeric compound as organic semiconductor wherein said compound contains a quinoid diheteroacene of the formula II, wherein 2 hydrogen atoms are replaced by open bonds, as a repeating unit.

21. Semiconductor device of claim 2, wherein the compound of the formula I is of the symmetry group $C_{2h}$.

22. Semiconductor device according to claim 4, wherein aryl is selected from the group consisting of phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl and benzothienyl.

23. Process for the preparation of an organic semiconductor device according to claim 8, which process comprises applying a compound of the formula I of claim 1 wherein at least one of R—$R_8$ contains an alkyl or alkylene chain of 4 or more carbon atoms.

24. The semiconductor device according to claim 1, wherein the semiconductor device comprises a semiconducting layer comprising the compound of formula (I).

\* \* \* \* \*